(12) United States Patent
Wang et al.

(10) Patent No.: US 9,394,358 B2
(45) Date of Patent: Jul. 19, 2016

(54) GENE SIGNATURE FOR PREDICTING PROGNOSIS OF PATIENTS WITH SOLID TUMORS

(71) Applicant: The United States of America, as represented by the Secretary, Department of Health and Human Services, Washington, DC (US)

(72) Inventors: Xin Wei Wang, Rockville, MD (US); Stephanie K. Roessler, Heidelberg (DE)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 25 days.

(21) Appl. No.: 14/252,005

(22) Filed: Apr. 14, 2014

(65) Prior Publication Data

US 2014/0220043 A1    Aug. 7, 2014

Related U.S. Application Data

(62) Division of application No. 13/127,701, filed as application No. PCT/US2009/063883 on Nov. 10, 2009, now Pat. No. 8,735,082.

(60) Provisional application No. 61/198,813, filed on Nov. 10, 2008.

(51) Int. Cl.
| | |
|---|---|
| *A61K 48/00* | (2006.01) |
| *C07K 16/18* | (2006.01) |
| *G01N 33/574* | (2006.01) |
| *C12N 15/113* | (2010.01) |
| *C12N 15/85* | (2006.01) |
| *C12N 15/86* | (2006.01) |
| *C12Q 1/68* | (2006.01) |

(52) U.S. Cl.
CPC .............. *C07K 16/18* (2013.01); *C12N 15/113* (2013.01); *C12N 15/85* (2013.01); *C12N 15/86* (2013.01); *C12Q 1/6886* (2013.01); *G01N 33/57415* (2013.01); *G01N 33/57438* (2013.01); *C12Q 1/6841* (2013.01); *C12Q 2600/112* (2013.01); *C12Q 2600/118* (2013.01); *C12Q 2600/136* (2013.01); *C12Q 2600/158* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 6,423,692 B2 | 7/2002 | Fine et al. | |
| 6,897,018 B1 | 5/2005 | Yuan et al. | |
| 6,974,667 B2 | 12/2005 | Horne et al. | |
| 2004/0005644 A1 | 1/2004 | Su et al. | |
| 2004/0029114 A1 | 2/2004 | Mack et al. | |
| 2005/0106616 A1 | 5/2005 | Yuan et al. | |
| 2005/0227255 A9 | 10/2005 | Yuan et al. | |
| 2006/0019256 A1 | 1/2006 | Clarke et al. | |
| 2006/0183141 A1 | 8/2006 | Chang et al. | |
| 2006/0194211 A1 | 8/2006 | Burczynski et al. | |
| 2007/0105133 A1 | 5/2007 | Clarke et al. | |
| 2007/0218512 A1 | 9/2007 | Strongin et al. | |
| 2008/0032299 A1 | 2/2008 | Burczynski et al. | |
| 2008/0206769 A1 | 8/2008 | Lau et al. | |
| 2008/0254456 A1 | 10/2008 | Lin | |
| 2008/0292546 A1 | 11/2008 | Clarke et al. | |
| 2009/0203051 A1 | 8/2009 | Gray et al. | |
| 2010/0113297 A1 | 5/2010 | Lidereau et al. | |

FOREIGN PATENT DOCUMENTS

| | | |
|---|---|---|
| DE | 198 13 835 | 9/1999 |
| WO | WO 99/43812 | 9/1999 |
| WO | WO 2004/029295 | 4/2004 |
| WO | WO 2004/081029 | 9/2004 |
| WO | WO 2005/108615 | 11/2005 |
| WO | WO 2006/016110 | 2/2006 |
| WO | WO 2007/030531 | 3/2007 |
| WO | WO 2007/030571 | 3/2007 |
| WO | WO 2007/063118 | 6/2007 |
| WO | WO 2008/070301 | 6/2008 |
| WO | WO 2008/079269 | 7/2008 |

OTHER PUBLICATIONS

Li et al, BMB Rep, 2009, 42:516-522.*
Lapinski et al, J Immunol, 2008, 181:2019-2027.*
Gura, Science, 1997, 278:1041-1042.*
Kaiser, Science, 2006, 313, 1370.*
Eck and Wilson, Goodman & Gilman's The Pharmacological basis of Therapeutics, 1996, McGraw-Hill, New York, NY. p. 77-101.*
Niidome and Huang, Gene Therapy, 2002, 9:1647-1652.*
Zhang et al, Molecular Therapy, 2012, 20:1298-1304.*
Gao et al, The AAPS Journal, 2007, 9:E92-E104.*
Parker et al, Expert Reviews in Molecular Medicine, 2003, 5:1-15.*
Affymetrix Inc., "Human Genome U133A Array Set", Affymetrix Product Catalog, p. 1, 2002.

(Continued)

*Primary Examiner* — Mark Halvorson
(74) *Attorney, Agent, or Firm* — Klaquist Sparkman, LLP

(57) ABSTRACT

Disclosed herein is a driver gene signature for predicting survival in patients with solid tumors, such as hepatocellular carcinoma (HCC) and breast cancer. The gene signature includes ten tumor-associated genes, SH2D4A, CCDC25, ELP3, DLC1, PROSC, SORBS3, HNRPD, PAQR3, PHF17 and DCK. A decrease in DNA copy number or mRNA expression of SH2D4A, CCDC25, ELP3, DLC1, PROSC and SORBS3 in solid tumors is associated with a poor prognosis, while a decrease in DNA copy number or mRNA expression of HNRPD, PAQR3, PHF17 and DCK in solid tumors is associated with a good prognosis. Methods of predicting the prognosis of a patient diagnosed with HCC or breast cancer by detecting expression of one of more tumor-associated genes, and methods of treating a patient diagnosed with HCC or breast cancer by administering an agent that alters expression or activity of one or more of the disclosed tumor-associated genes, are described.

5 Claims, 13 Drawing Sheets

(56) References Cited

OTHER PUBLICATIONS

Fan et al., "RKTG Sequesters B-Raf to the Golgi Apparatus and Inhibits the Proliferation and Tumorigenicity of Human Malignant Melanoma Cells," *Carcinogenesis*, vol. 29(6):1157-1163, 2008.

Karbownik et al., "Increased Expression of mRNA Specific for Thymidine Kinase, Deoxycytidine Kinase or Thymidine Phosphorylase in Human Papillary Thyroid Carcinoma," *Cancer Lett.*, vol. 225:267-273, 2005.

Lee et al., "Classification and Prediction of Survival in Hepatocellular Carcinoma by Gene Expression Profiling," *Hepatology*, vol. 40(3):667-676, 2004.

Lee et al., "Analysis of Gene Expression Profiles of Hepatocellular Carcinomas with regard to F-fluorodeoxyglucose Uptake Pattern on Positron Emission Tomography," *Eur. J. Nucl. Med. Mol. Imaging*, vol. 31(12):1621-1630, 2004.

Paek et al., "RNA-Binding Protein hnRNP D Modulates Internal Ribosome Entry Site-Dependent Translation of Hepatitis C Virus RNA," *J. Virol.*, vol. 82(24):12082-12093, 2008.

Pai et al., "Prospects of RNA Interference Therapy for Cancer," *Gene Therapy*, vol. 13:464-477, 2006.

Patil et al., "Array-based Comparative Genomic Hybridization Reveals Recurrent Chromosomal Aberrations and Jab 1 as a Potential Target for 8q Gain in Hepatocellular Carcinoma," *Carcinogenesis*, vol. 26(12):2050-2057, 2005.

Patrakka et al., "Expression and Subcellular Distribution of Novel Glomerulus-Associated Proteins Dendrin, Ehd3, Sh2d4a, Plekhh2, and 2310066E14Rik," *J. Am. Soc. Nephrol.*, vol. 18:689-697, 2007.

Roessler et al., "Future of Molecular Profiling of Human Hepatocellular Carcinoma," *Future Oncol.*, vol. 3(4):429-439, 2007.

Rubanyi, "The Future of Human Gene Therapy," *Mol. Aspects of Medicine*, vol. 22:113-142, 2001.

Ryther et al., "siRNA Therapeutics: Big Potential from Small RNAs," *Gene Therapy*, vol. 12:5-11, 2005.

Shi et al., "Association Between Single Nucleotide Polymorphisms in Deoxycytidine Kinase and Treatment Response Among Acute Myeloid Leukaemia Patients," *Pharmacogenetics*, vol. 14:759-768, 2004.

Spasokoukotskaja et al., "Expression of Deoxycytidine Kinase and Phosphorylation of 2-Chlorodeoxyadenosine in Human Normal and Tumour Cells and Tissues," *Eur. J. Cancer*, vol. 31A(2):202-208, 1995.

Xue et al, "DLC1 is a Chromosome 8p Tumor Suppressor Whose Loss Promotes Hepatocellular Carcinoma," *Genes Dev.*, vol. 22:1439-1444, 2008.

Yuan, et al., "Cloning, Characterization, and Chromosomal Localization of a Gene Frequently Deleted in Human Liver Cancer (DLC-1) Homologous to Rat *Rho*GAP," *Cancer Res.*, vol. 58:2196-2199, 1998.

Zhou et al., "Restoration of DLC-1 Gene Expression Induces Apoptosis and Inhibits Both Cell Growth and Tumorigenicity in Human Hepatocellular Carcinoma Cells," *Oncogene*, vol. 23:1308-1313, 2004.

Zhou et al., "Jade-1, a Candidate Renal Tumor Suppressor that Promotes Apoptosis," *Proc. Natl. Acad. Sci. USA*, vol. 102(31):11035-11040, 2005.

Partial European Search Report for European Application No. 12 18 8475, dated Dec. 4, 2013.

* cited by examiner

FIG. 1A
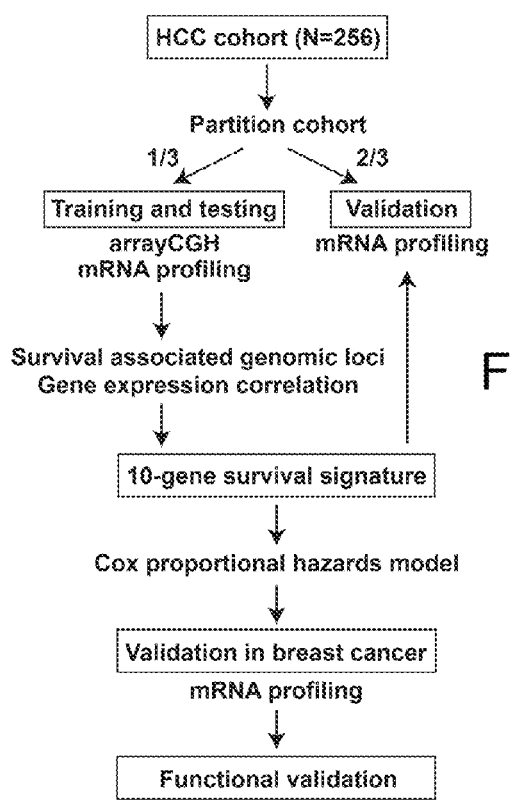
FIG. 1B
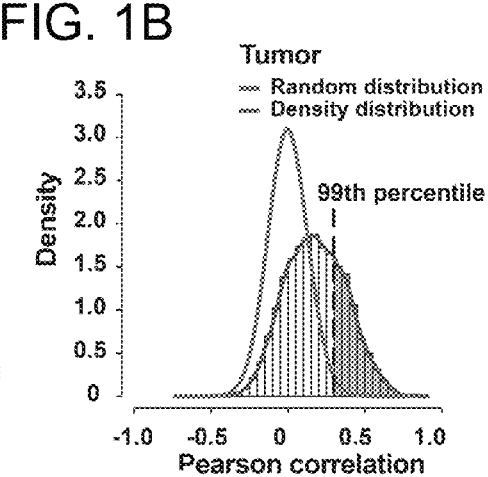
FIG. 1C
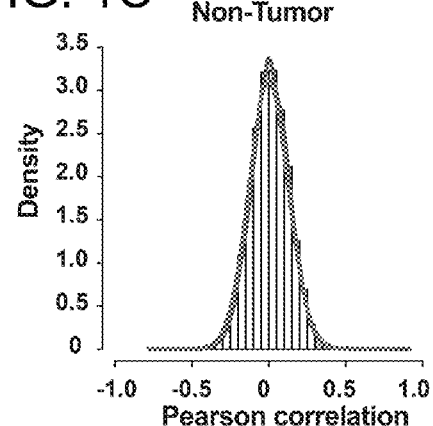
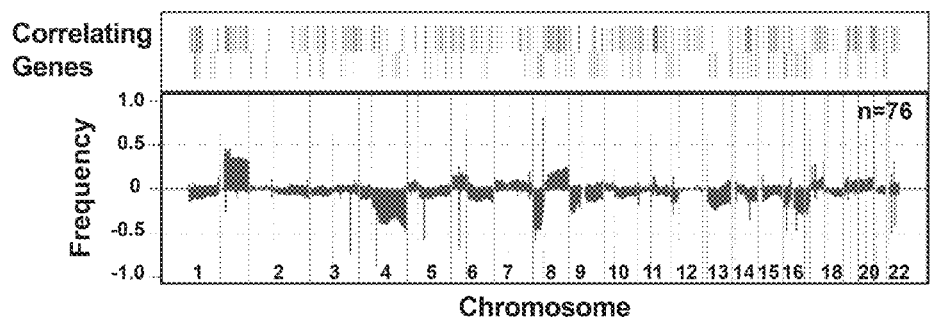
FIG. 1D

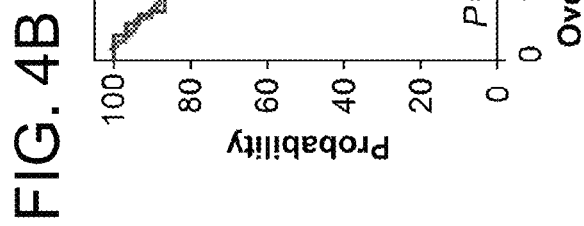
FIG. 4A  FIG. 4B
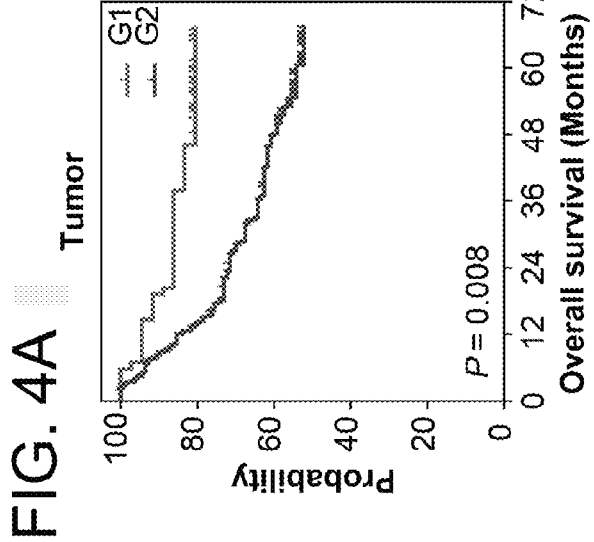
FIG. 4C
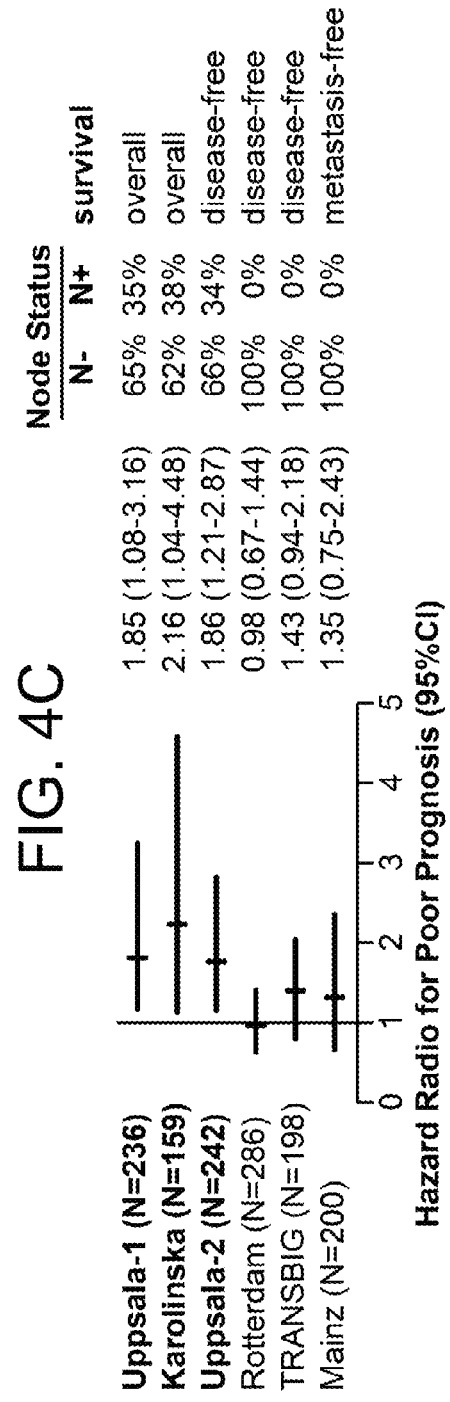

CCP

LDA

NC

SVM

GENE SIGNATURE FOR PREDICTING PROGNOSIS OF PATIENTS WITH SOLID TUMORS

CROSS REFERENCE TO RELATED APPLICATIONS

This is a divisional of U.S. application Ser. No. 13/127,701, filed May 4, 2011, issued as U.S. Pat. No. 8,735,082 on May 27, 2014, which is the U.S. National Stage of International Application No. PCT/US2009/063883, filed Nov. 10, 2009, published in English under PCT Article 21(2), which claims the benefit of U.S. Provisional Application No. 61/198,813, filed Nov. 10, 2008. The above-listed applications are herein incorporated by reference in their entirety.

FIELD

This disclosure relates to the field of solid tumors and in particular, to methods for predicting the prognosis of patients with solid tumors, such as hepatocellular carcinoma or breast cancer, using a driver gene signature.

BACKGROUND

A progressive sequence of somatic mutations and epigenetic changes of oncogenes or tumor suppressor genes in one single cell are believed to cause tumor development. This initial cell proliferates and due to genomic instability, the cells accumulate genomic changes which lead to clonal expansion and tumor development (Hanahan and Weinberg, *Cell* 100:57-70, 2000). These genomic changes are irreversible and specific to tumor cells. Therefore, they provide ideal targets for the development of new therapies. However, high genomic instability in tumors causes the accumulation of genomic aberrations that do not contribute do tumor progression. In addition, cancer is a very heterogeneous disease because changes in many different cellular pathways can lead to tumor development. Therefore, it is important to distinguish between 'driver' mutations which are functionally important and 'passenger' mutations which do not provide a selective advantage to the tumor cells.

Hepatocellular carcinoma (HCC) is the most frequent malignant tumor in the liver and the third leading cause of cancer death worldwide (Parkin et al., *CA Cancer J. Clin.* 55:74-108, 2005). Various etiologies have been shown to underlie HCC development, including hepatitis B virus (HBV) and hepatitis C virus (HCV) infection, chronic alcohol consumption, ingestion of aflatoxin B1 contaminated food as well as inherited hemochromatosis (Farazi and DePinho, *Nat. Rev. Cancer* 6:674-687, 2006). Surgical resection is the only curative treatment of HCC, but eligibility is sparse because most patients present with advanced disease (McCormack et al., *Eur. J. Gastroenterol. Hepatol.* 17:497-503, 2005). Systemic chemotherapy has been shown to be ineffective and tumor recurrence rate after surgical resection is high due to relapse and metastasis (Llovet et al., *Semin. Liver Dis.* 25:181-200, 2005). Therefore, the development of new drugs will be crucial to prevent relapse and to prolong patient survival.

In addition, despite considerable progress during the last few years, the molecular mechanisms and signaling pathways underlying HCC development and progression are still poorly understood. This is likely because HCC, like most other solid tumors, is very heterogeneous in terms of clinical presentation and gene expression patterns.

SUMMARY

Solid tumors, such as HCC tumors, are genetically unstable, leading to a number of genetic mutations that do not contribute to tumor progression. This type of genetic aberration is referred to as a "passenger" mutation. Described herein is an integrative approach to identify functionally relevant "driver" mutations in solid tumors. Disclosed herein is the identification of a driver gene signature that can be used to predict clinical outcome, such as survival, of patients with solid tumors such as HCC and breast cancer patients. The signature includes ten genes, SH2D4A, CCDC25, ELP3, DLC1, PROSC, SORBS3, HNRPD, PAQR3, PHF17 and DCK. In some embodiments, a decrease in DNA copy number or mRNA expression of SH2D4A, CCDC25, ELP3, DLC1, PROSC and SORBS3 in solid tumors is associated with a poor prognosis, while a decrease in DNA copy number or mRNA expression of HNRPD, PAQR3, PHF17 and DCK in solid tumors is associated with a good prognosis.

Provided herein is a method of predicting the prognosis of a subject diagnosed with HCC. In particular examples, the method includes detecting expression of two or more HCC-associated genes in a tumor sample obtained from the subject, and comparing expression of the HCC-associated genes in the tumor sample to a control. As disclosed herein, the HCC-associated genes include SH2D4A, CCDC25, ELP3, DLC1, PROSC, SORBS3, HNRPD, PAQR3, PHF17 and DCK. Also provided is a method of predicting the prognosis of a subject with breast cancer, by detecting expression of two or more tumor-associated genes in a tumor sample obtained from the subject, and comparing expression of the tumor-associated genes in the tumor sample to a control. As disclosed herein, the tumor-associated genes include SH2D4A, CCDC25, ELP3, DLC1, PROSC, SORBS3, HNRPD, PAQR3, PHF17 and DCK.

In some embodiments of the methods, a decrease in expression of SH2D4A, CCDC25, ELP3, DLC1, PROSC and/or SORBS3 in the tumor sample relative to the control indicates a poor prognosis. In some embodiments, an increase in expression of HNRPD, PAQR3, PHF17 and/or DCK in the tumor sample relative to the control indicates a poor prognosis. In some examples, the control is adjacent non-tumor tissue from the subject. A poor prognosis refers to any negative clinical outcome, such as a decrease in the likelihood of survival, a decrease in the time of survival or an increase in the risk of metastasis.

Further provided are methods of treating HCC or breast cancer in a subject by administering to the subject a therapeutically effective amount of an agent that alters expression or activity of at least one tumor-associated molecule selected from SH2D4A, CCDC25, ELP3, DLC1, PROSC, SORBS3, HNRPD, PAQR3, PHF17 and DCK. Also provided are methods of treating HCC or breast cancer in a subject by administering to the subject a therapeutically effective amount of an isolated nucleic acid molecule encoding a tumor-associated gene, such as SH2D4A, CCDC25, ELP3, DLC1, PROSC or SORBS3. In particular examples, the nucleic acid molecule encodes SH2D4A or SORBS3.

Also provided herein is a method of identifying an agent for use in treating a solid tumor such as HCC or breast cancer. The method includes contacting a solid tumor cell (such as HCC or breast cancer cell) with one or more candidate agents under conditions sufficient for the one or more candidate agents to alter expression or activity of at least one HCC-associated molecule; detecting expression or activity of the at least one HCC-associated molecule in the presence of the one or more candidate agents; and comparing expression or activity of the at least one HCC-associated molecule in the presence of the one or more candidate agents to a control. An increase in expression or activity of SH2D4A, CCDC25, ELP3, DLC1, PROSC or SORBS3, and/or a decrease in expression or activity of HNRPD, PAQR3, PHF17 or DCK, relative to the control indicates that the one or more candidate agents is of use to treat a solid tumor such as HCC or breast cancer.

Further provided is an array comprising probes or antibodies specific for two or more HCC-associated genes or proteins, such as two or more of SH2D4A, CCDC25, ELP3, DLC1, PROSC, SORBS3, HNRPD, PAQR3, PHF17 and DCK.

The foregoing and other objects and features of the disclosure will become more apparent from the following detailed description, which proceeds with reference to the accompanying figures.

BRIEF DESCRIPTION OF THE FIGURES

FIG. 1A is a schematic overview of the study design. FIG. 1B is a density histogram showing the distribution of the Pearson correlation coefficients of gene expression and array-CGH data from 60 tumor tissues. Gene expression and copy number data of 10841 genes was used. The left curve represents 1000-fold random distribution and the right curve represents the density distribution of the Pearson correlation coefficient. FIG. 1C is a density histogram showing the Pearson correlation coefficient of the gene expression of the non-tumor tissue and paired arrayCGH data of the cancerous tissue. The random distribution curve and the density distribution curve of the Pearson correlation coefficient overlap. FIG. 1D is a graph showing the frequency of significant increases in genome copy number plotted as a function of genome location for 76 clinical specimens. Positive values indicate frequencies of samples showing copy number increases [log 2(copy number)>0.5] and negative values indicate frequencies of samples showing copy number decreases [log 2(copy number)<−0.5]. The upper panel shows the positions of correlating genes which are more than two-fold up- (top set of lines) or down-regulated (bottom set of lines) compared to normal liver.

FIG. 4A is a graph showing Kaplan-Meier overall survival on the independent validation cohort 2 by predicted classification of G1 and G2 by Support Vector Machines (SVM). FIG. 4B is a graph showing Kaplan-Meier overall survival based on the predicted classification of G1 and G2 by gene expression of the non-tumor tissue of the validation cohort by SVM. FIG. 4C is a Forest plot of the hazard ratios for poor survival of six breast cancer studies with varying percentage of node-negative patients. HR (95% CI), hazard ratio (95% confidence interval); N−, node-negative status; N+; node-positive status.

DETAILED DESCRIPTION

I. Introduction

Figure 2A:
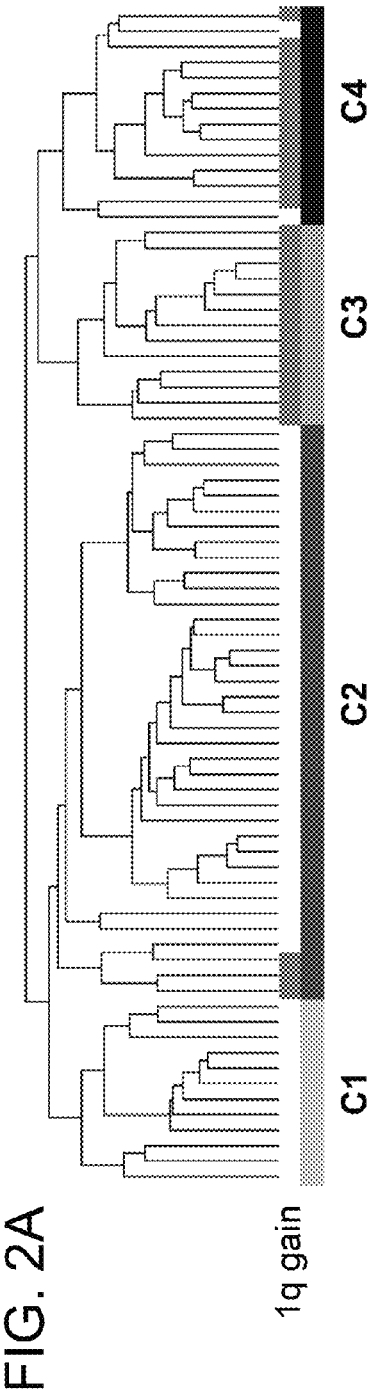
FIG. 2A is a graph showing unsupervised hierarchical clustering of the weighted genomic aberration profile of array-CGH data (N=76), which revealed clusters C1, C2, C3 and C4.

Like most other solid tumors, hepatocellular carcinoma (HCC) is very heterogenous in terms of clinical presentation and genomic profiling. The high heterogeneity is caused by abnormalities in many different cellular pathways which lead to tumor development. In addition, the genomic instability of the tumor cells causes the accumulation of genomic aberrations which do not contribute do tumor progression. Therefore, it is important to distinguish between 'driver' mutations which are functionally important and 'passenger' genes which do not provide a selective advantage to the tumor cells. Described herein is an integrative approach applying array-based comparative genomic hybridization (arrayCGH) and gene expression profiling of HCC tumor samples to identify cancer 'driver' genes in HCC. Although arrayCGH showed multiple regions of gene amplification and loss of heterozygosity, only loss regions were associated with survival. Correlation analysis of gene expression and DNA copy number led to the identification of ten candidate cancer driver genes which serve as a gene signature to predict clinical outcome of patients with HCC. Six of these genes are located in loss regions of chromosome 8p and are associated with poor coutcome, while four genes are located in loss regions of 4q and are associated with good prognosis. The 10-gene signature is also predictive of clinical outcome of breast cancer patients with mixed node status. Thus, described herein is the identification of a unique gene signature which is able to predict survival and patient outcome in solid tumors, including HCC and breast cancer. In addition, the ten genes are potential drug targets for the development of new therapeutic agents for the treatment of solid tumors.

II. Abbreviations

1NN 1-Nearest Neighbor
3NN 3-Nearest Neighbor
AFP Alphafetoprotein
ALT Alanine transferase
BCLC Barcelona clinic liver cancer
CBS Circular binary segmentation
CCDC25 Coiled-coil domain containing 25
CCP Compound covariate predictor
CGH Comparative genomic hybridization
CI Confidence interval
CLIP Cancer of the Liver Italian Program
DCK Deoxycytidine kinase
DLC1 Deleted in liver cancer 1
DLP Diagonal linear discriminant
DLRS Derivative log ratio spread
DNA Deoxyribonucleic acid
dsDNA Double-stranded DNA
ELP3 Elongation protein 3
GEO Gene expression omnibus
HBV Hepatitis B virus
HCC Hepatocellular carcinoma
HCV Hepatitis C virus
HNRPD Heterogeneous nuclear ribonucleoprotein D
HR Hazard ratio
LDA Linear discriminant analysis
MDS Multidimensional analysis
MIAME Minimum information about a microarray experiment
miRNA MicroRNA
mRNA Messenger ribonucleic acid
NC Nearest centroid
NUSE Normalized unsealed standard error
PAQR3 Progestin and adipoQ receptor family member III
PCR Polymerase chain reaction
PHF17 PHD finger protein 17
PROSC Proline synthetase co-transcribed homolog
RLE Relative log expression
RMA Robust multiarray average
RNA Ribonucleic acid
RT Reverse transcriptase
SEM Standard error of the mean
SH2D4A SH2 domain containing 4A
shRNA Short hairpin RNA
siRNA Short interfering RNA
SORBS3 Sorbin and SH3 domain containing 3
SVM Support vector machines
TNM Tumor node metastasis
TSG Tumor suppressor gene

III. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjunctive therapy: A treatment used in combination with a primary treatment to improve the effects of the primary treatment. For example, adjunctive therapy includes chemotherapy that is administered following surgical resection of cancerous tissue.

Administration: To provide or give a subject an agent, such as a chemotherapeutic agent, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Agent: Any protein, nucleic acid molecule, compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject).

Antibody: A polypeptide including at least a light chain or heavy chain immunoglobulin variable region which specifically recognizes and binds an epitope of an antigen, such as SH2D4A, CCDC25, ELP3, DLC1, PROSC, SORBS3, HNRPD, PAQR3, PHF17 or DCK, or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Antibodies of the present disclosure include those that are specific for SH2D4A, CCDC25, ELP3, DLC1, PROSC, SORBS3, HNRPD, PAQR3, PHF17 or DCK.

The term antibody includes intact immunoglobulins, as well the variants and portions thereof, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds RET will have a specific $V_H$ region and the $V_L$ region sequence, and thus specific CDR sequences. Antibodies with different specificities (such as different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen, which are then purified from the mammal's serum.

A "chimeric antibody" has framework residues from one species, such as human, and CDRs (which generally confer antigen binding) from another species, such as a murine antibody that specifically binds SH2D4A, CCDC25, ELP3, DLC1, PROSC, SORBS3, HNRPD, PAQR3, PHF17 or DCK.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one example, all the CDRs are from the donor immunoglobulin in a humanized immunoglobulin. Constant regions need not be present, but if they are, they are substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585,089).

Antisense compound: Refers to an oligomeric compound that is at least partially complementary to the region of a target nucleic acid molecule to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression. In some examples, the target nucleic acid molecule is HNRPD, PAQR3, PHF17 or DCK.

Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound.

Antisense oligonucleotide: As used herein, an "antisense oligonucleotide" is a single-stranded antisense compound that is a nucleic acid-based oligomer. An antisense oligonucleotide can include one or more chemical modifications to the sugar, base, and/or internucleoside linkages. Generally, antisense oligonucleotides are "DNA-like" such that when the antisense oligonucleotide hybridizes to a target mRNA, the duplex is recognized by RNase H (an enzyme that recognizes DNA:RNA duplexes), resulting in cleavage of the mRNA.

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe or antibody) will occur on the array a plurality of times (such as twice), for instance to provide internal controls. The number of addressable locations on the array can vary, for example from at least four, to at least 9, at least 10, at least 14, at least 15, at least 20, at least 30, at least 50, at least 75, at least 100, at least 150, at least 200, at least 300, at least 500, least 550, at least 600, at least 800, at least 1000, at least 10,000, or more. In a particular example, an array includes 5-100 addressable locations, such as 5-50 addressable locations. In particular examples, an array consists essentially of probes or primers or antibodies (such as those that permit amplification or detection) specific for SH2D4A, CCDC25, ELP3, DLC1, PROSC, SORBS3, HNRPD, PAQR3, PHF17 and/or DCK, and in some examples, also 1 to 10 control molecules (such as housekeeping genes).

In particular examples, an array includes nucleic acid molecules, such as oligonucleotide sequences that are at least 15 nucleotides in length, such as about 15-40 nucleotides in length.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including nucleic acids to which proteins are bound, or vice versa. In some examples, an array contains antibodies to at least two, at least three, at least four, at least five, or 10 different HCC-associated molecules, and in some examples also 1 to 10 housekeeping genes.

Binding or Stable Binding: An association between two substances or molecules, such as the hybridization of one nucleic acid molecule to another (or itself), the association of an antibody with a peptide, or the association of a protein with another protein or nucleic acid molecule. An oligonucleotide molecule binds or stably binds to a target nucleic acid molecule if a sufficient amount of the oligonucleotide molecule forms base pairs or is hybridized to its target nucleic acid molecule, to permit detection of that binding. "Preferentially binds" indicates that one molecule binds to another with high affinity, and binds to heterologous molecules at a low affinity.

Binding can be detected by any procedure known to one skilled in the art, such as by physical or functional properties of the target:oligonucleotide complex. For example, binding can be detected functionally by determining whether binding has an observable effect upon a biosynthetic process such as expression of a gene, DNA replication, transcription, translation, and the like.

Physical methods of detecting the binding of complementary strands of nucleic acid molecules, include but are not limited to, such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is a rapid increase in absorption at a characteristic temperature as the oligonucleotide (or analog) and target disassociate from each other, or melt. In another example, the method involves detecting a signal, such as a detectable label, present on one or both nucleic acid molecules (or antibody or protein as appropriate). Methods of detecting binding of an antibody to a protein are routine, such as Western blotting.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Breast cancer: A type of cancer that forms in the tissues of the breast, typically in the ducts and lobules. In some embodiments, a patient with breast cancer is node-positive, meaning the breast cancer has spread to the lymph nodes.

Cancer: The "pathology" of cancer includes all phenomena that compromise the well-being of the subject. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc. "Metastatic disease" refers to cancer cells that have left the original tumor site and migrate to other parts of the body, for example via the bloodstream or lymph system.

Chronic viral infection: A viral infection of long duration or that recurs over a long period of time. Many cases of HCC are secondary to chronic hepatitis virus infection, such as chronic hepatitis infection, such as hepatitis B virus or hepatitis C virus infection.

Cirrhosis: A chronic progressive disease of the liver characterized by the replacement of healthy cells with scar tissue. Many cases of HCC are secondary to cirrhosis of the liver. Cirrhosis can be caused by a variety of factors, such as alcoholism (chronic alcohol consumption), exposure to (e.g. ingestion of) aflatoxin (such as aflatoxin B1), or genetic disorders, such as inherited hemochromatosis.

Chemotherapeutic Agent or Chemotherapy: Any chemical agent with therapeutic usefulness in the treatment of diseases characterized by abnormal cell growth. Such diseases include tumors, neoplasms, and cancer. In one example, a chemotherapeutic agent is an agent of use in treating HCC. In another example, a chemotherapeutic agent is an agent of use in treating breast cancer. In one example, a chemotherapeutic agent is a radioactive compound. One of skill in the art can readily identify a chemotherapeutic agent of use (see for example, Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., 2000 Churchill Livingstone, Inc; Baltzer and Berkery. (eds): Oncology Pocket Guide to Chemotherapy, 2nd ed. St. Louis, Mosby-Year Book, 1995; Fischer Knobf, and Durivage (eds): The Cancer Chemotherapy Handbook, 4th ed. St. Louis, Mosby-Year Book, 1993). Exemplary chemotherapeutic agents used for treating cancer include carboplatin, cisplatin, paclitaxel, docetaxel, doxorubicin, epirubicin, topotecan, irinotecan, gemcitabine, iazofurine, gemcitabine, etoposide, vinorelbine, tamoxifen, valspodar, cyclophosphamide, methotrexate, fluorouracil, mitoxantrone and vinorelbine. Combination chemotherapy is the administration of more than one agent to treat cancer. Chemotherapeutic agents in some examples include those that increase the expression or activity of SH2D4A, CCDC25, ELP3, DLC1, PROSC or SORBS3, or decrease the expression or activity of HNRPD, PAQR3, PHF17 or DCK.

Clinical outcome: Refers to the health status of a patient following treatment for a disease or disorder, or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Coiled-coil domain containing 25 (CCDC25): The CCD25 gene encodes a 208 amino acid protein of unknown function. CCD25 is also known as FLJ10853. In particular examples, an increase in expression of CCD25 in HCC, relative to a control, indicates a good prognosis for the HCC or breast cancer patient. The term "CCD25" includes a CCD25 gene, cDNA, mRNA, or protein.

CCD25 sequences are publically available. For example, GenBank Accession No. AC104997 (deposited Mar. 15, 2002) discloses a human CCD25 gene sequence. GenBank Accession Nos. NM_018246.2 and NP_060716.2 (each deposited Jun. 14, 2006) disclose human CCD25 mRNA and protein sequences, respectively. One skilled in the art will appreciate that CCD25 nucleic acid and protein molecules can vary from those publicly available, while still retaining CCD25 biological activity (e.g., increased expression correlates with a good prognosis for a solid tumor patient).

Colon cancer: Cancer that forms in the tissues of the colon. Most colon cancers are adenocarcinomas (cancers that begin in cells that make and release mucus and other fluids).

Comparative genomic hybridization (CGH): A molecular-cytogenetic method for the analysis of copy number changes (gains/losses) in the DNA content of cells, such as tumor cells. The method is based on the hybridization of fluorescently labeled tumor DNA (such as, Fluorescein—FITC) and normal DNA (such as, Rhodamine or Texas Red) to normal human metaphase preparations. Using methods known in the art, such as epiflourescence microscopy and quantitative image analysis, regional differences in the fluorescence ratio of tumor versus control DNA can be detected and used for identifying abnormal regions in the tumor cell genome. CGH detects unbalanced chromosomes changes. Structural chromosome aberrations, such as balanced reciprocal translocations or inversions, are not detected, as they do not change the copy number.

In one example, CGH includes the following steps. DNA from tumor tissue and from normal control tissue (reference) is labeled with different detectable labels, such as two different fluorophores. After mixing tumor and reference DNA along with unlabeled human cot 1 DNA to suppress repetitive DNA sequences, the mix is hybridized to normal metaphase chromosomes or, for array- or matrix-CGH, to a slide containing hundreds or thousands of defined DNA probes. The (fluorescence) color ratio along the chromosomes is used to evaluate regions of DNA gain or loss in the tumor sample.

Complementarity and percentage complementarity: Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide molecule remains detectably bound to a target nucleic acid sequence under the required conditions.

Complementarity is the degree to which bases in one nucleic acid strand base pair with the bases in a second nucleic acid strand. Complementarity is conveniently described by percentage, that is, the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

In the present disclosure, "sufficient complementarity" means that a sufficient number of base pairs exist between an oligonucleotide molecule and a target nucleic acid sequence to achieve detectable binding. When expressed or measured by percentage of base pairs formed, the percentage complementarity that fulfills this goal can range from as little as about 50% complementarity to full (100%) complementary. In general, sufficient complementarity is at least about 50%, for example at least about 75% complementarity, at least about 90% complementarity, at least about 95% complementarity, at least about 98% complementarity, or even at least about 100% complementarity.

A thorough treatment of the qualitative and quantitative considerations involved in establishing binding conditions that allow one skilled in the art to design appropriate oligonucleotides for use under the desired conditions is provided by Beltz et al. *Methods Enzymol.* 100:266-285, 1983, and by Sambrook et al. (ed.), *Molecular Cloning: A Laboratory Manual,* 2nd ed., vol. 1-3, Cold Spring Harbor Laboratory Press, Cold Spring Harbor, N.Y., 1989.

Consists essentially of: In the context of the present disclosure, "consists essentially of" indicates that the expression of additional HCC-associated genes can be evaluated, but not more than ten additional HCC-associated genes. In some examples, "consist essentially of" indicates that no more than 5 other molecules are evaluated, such as no more than 4, 3, 2, or 1 other molecules. In some examples, fewer than the recited molecules are evaluated, but not less than 5, 4, 3, 2 or 1 fewer molecules. In some examples, the expression of one or more controls is evaluated, such as a housekeeping protein or rRNA (such as 18S RNA, beta-microglobulin, GAPDH, and/or 18S rRNA). In this context "consist of" indicates that only the expression of the stated molecules are evaluated; the expression of additional molecules is not evaluated.

Contacting: Placement in direct physical association, including both solid or liquid forms. Contacting an agent with a cell can occur in vitro by adding the agent to isolated cells or in vivo by administering the agent to a subject.

Control: A "control" refers to a sample or standard used for comparison with an experimental sample, such as a tumor sample obtained from a patient with HCC or breast cancer. In some embodiments, the control is a sample obtained from a healthy patient or a non-tumor tissue sample obtained from a patient diagnosed with HCC or breast cancer. In some embodiments, the control is a historical control or standard reference value or range of values (i.e. a previously tested control sample, such as a group of HCC or breast cancer patients with poor prognosis, or group of samples that represent baseline or normal values, such as the level of HCC-associated genes in non-tumor tissue).

Decrease: To reduce the quality, amount, or strength of something. In one example, a therapy decreases a tumor (such as the size of a tumor, volume of a tumor, the number of tumors, the metastasis of a tumor, or combinations thereof), or one or more symptoms associated with a tumor, for example as compared to the response in the absence of the therapy. In a particular example, a therapy decreases the size of a tumor, volume of a tumor, the number of tumors, the metastasis of a tumor, or combinations thereof, subsequent to the therapy, such as a decrease of at least 10%, at least 20%, at least 50%, or even at least 90%. Such decreases can be measured using the methods disclosed herein. In additional examples, an increase or decrease in expression of one or more HCC-associated genes results in a decrease in survival. As used herein, a "decrease in survival" refers to a decrease in the length of time before death of a patient, or an increase in the risk of death for the patient.

Deleted in liver cancer 1 (DLC1): The DLC1 gene is deleted in primary HCC tumors and maps to 8p22-p21.3, a region frequently deleted in solid tumors. DLC1 is a candidate tumor suppressor gene for human liver cancer, as well as for prostate, lung, colorectal, and breast cancers. Alternative splicing at this locus results in several transcript variants encoding different isoforms. DLC1 is also known as HP, ARHGAP7, STARD12, FLJ21120 and p122-RhoGAP. In particular examples, an increase in expression of DLC1 in HCC or breast cancer, relative to a control, indicates a good prognosis for the HCC or breast cancer patient. The term "DLC1" includes a DLC1 gene, cDNA, mRNA, or protein.

DLC1 sequences are publically available. For example, GenBank Accession No. AC015641 (deposited Apr. 14, 2002) discloses a human DLC1 gene sequence. GenBank Accession Nos. NM_182643.1 and NP_872584.1 (each deposited Jul. 24, 2003) disclose human DLC1 isoform 1 mRNA and protein sequences, respectively. GenBank Accession Nos. NM_006094.3 and NP_006085.2 (each deposited Jul. 24, 2003) disclose human DLC1 isoform 2 mRNA and protein sequences, respectively. GenBank Accession Nos. NM_024767.2 and NP_079043.2 (each deposited Jul. 24, 2003) disclose human DLC1 isoform 3 mRNA and protein sequences, respectively. One skilled in the art will appreciate that DLC1 nucleic acid and protein molecules can vary from those publicly available, while still retaining DLC1 biological activity (e.g., increased expression correlates with a good prognosis for a solid tumor patient).

Deoxycytidine kinase (DCK): The DCK protein is required for the phosphorylation of several deoxyribonucleosides and their nucleoside analogs. Deficiency of DCK is associated with resistance to antiviral and anticancer chemotherapeutic agents. Conversely, increased deoxycytidine kinase activity is associated with increased activation of these compounds to cytotoxic nucleoside triphosphate derivatives. DCK is also known as MGC117410 and MGC138632. In particular examples, a decrease in expression of DCK in HCC or breast cancer, relative to a control, indicates a good prognosis for the HCC or breast cancer patient. The term "DCK" includes a DCK gene, cDNA, mRNA, or protein.

DCK sequences are publically available. For example, GenBank Accession No. AC093851 (deposited Sep. 25, 2002) discloses a human DCK gene sequence. GenBank Accession Nos. NM_000788.2 (deposited Jul. 29, 2008) and NP_000779.1 (deposited Mar. 24, 1999) disclose human DCK mRNA and protein sequences, respectively. One skilled in the art will appreciate that DCK nucleic acid and protein molecules can vary from those publicly available, while still retaining DCK biological activity (e.g., decreased expression correlates with a good prognosis for a solid tumor patient).

Detecting expression of a gene product: Determining of a level expression in either a qualitative or quantitative manner can detect nucleic acid or protein. Exemplary methods include microarray analysis, RT-PCR, Northern blot, Western blot, and mass spectrometry.

Diagnosis: The process of identifying a disease by its signs, symptoms and results of various tests. The conclusion reached through that process is also called "a diagnosis." Forms of testing commonly performed include blood tests, medical imaging, urinalysis, and biopsy.

Differential expression or altered expression: A difference, such as an increase or decrease, in the conversion of the information encoded in a gene (such as a HCC-associated gene) into messenger RNA, the conversion of mRNA to a protein, or both. In some examples, the difference is relative to a control or reference value (or range of values), such as the average expression value of a group of subjects, such as a group of HCC or breast cancer patients with poor prognosis. The difference can also be relative to non-tumor tissue from the same subject or a healthy subject. Detecting differential expression can include measuring a change in gene or protein expression, such as a change in expression of one or more HCC-associated genes.

Downregulated or decreased: When used in reference to the expression of a nucleic acid molecule (such as a HCC-associated nucleic acid molecule), refers to any process which results in a decrease in production of a gene product. A gene product can be RNA (such as microRNA, mRNA, rRNA, tRNA, and structural RNA) or protein. Therefore, gene downregulation or deactivation includes processes that decrease transcription of a gene or translation of mRNA.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability.

Gene downregulation includes any detectable decrease in the production of a gene product. In certain examples, production of a gene product decreases by at least 2-fold, for example at least 3-fold or at least 4-fold, as compared to a control (such an amount of gene expression in a normal cell or in comparison to a reference value).

Elongation protein 3 (ELP3): The ELP3 protein is one of three proteins that make up the RNA polymerase II elongator complex, a component of the RNA polymerase II holoenzyme. ELP3 possesses histone acetyltransferase activity and is involved in transcriptional elongation. The elongator complex is thought to play a role in chromatin remodeling and acetylation of histones H3 and H4. ELP3 is also known as human elongation protein 3 homolog (hELP3), KAT9 and FLJ10422. In particular examples, an increase in expression of ELP3 in HCC or breast cancer, relative to a control, indicates a good prognosis for the HCC or breast cancer patient. The term "ELP3" includes a ELP3 gene, cDNA, mRNA, or protein.

ELP3 sequences are publically available. For example, GenBank Accession No. AC019031 (deposited Nov. 18, 2001) discloses a human ELP3 gene sequence. GenBank Accession Nos. NM_018091.5 (deposited May 10, 2008) and NP_060561.3 (deposited Oct. 7, 2002) disclose human ELP3 mRNA and protein sequences, respectively. One skilled in the art will appreciate that ELP3 nucleic acid and protein molecules can vary from those publicly available, while still retaining ELP3 biological activity (e.g., increased expression correlates with a good prognosis for a solid tumor patient).

Esophageal cancer: Cancer that forms in tissues lining the esophagus (the muscular tube through which food passes from the throat to the stomach). Two types of esophageal cancer are squamous cell carcinoma (cancer that begins in flat cells lining the esophagus) and adenocarcinoma (cancer that begins in cells that make and release mucus and other fluids).

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced. In an example, gene expression can be monitored to diagnosis and/or prognosis a subject with HCC or breast cancer, such as predict a subject's survival time.

The expression of a nucleic acid molecule can be altered relative to a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or sub-domain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard. Controls or standards for comparison to a sample, for the determination of differential expression, include samples believed to be normal (in that they are not altered for the desired characteristic, for example a sample from a subject who does not have cancer, such as HCC or breast cancer) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

Expression vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes.

Gene expression profile (or fingerprint): Differential or altered gene expression can be detected by changes in the detectable amount of gene expression (such as cDNA or mRNA) or by changes in the detectable amount of proteins expressed by those genes. A distinct or identifiable pattern of gene expression, for instance a pattern of high and low expression of a defined set of genes or gene-indicative nucleic acids such as ESTs; in some examples, as few as one or two genes provides a profile, but more genes can be used in a profile, for example at least 3, at least 4, at least 5, at least 6, or at least 10. A gene expression profile (also referred to as a fingerprint) can be linked to a tissue or cell type (such as HCC or breast cancer), to a particular stage of normal tissue growth or disease progression (for example, node-positive breast cancer), or to any other distinct or identifiable condition that influences gene expression in a predictable way. Gene expression profiles can include relative as well as absolute expression levels of specific genes, and can be viewed in the context of a test sample compared to a baseline or control sample profile (such as a sample from a subject who does not have HCC or breast cancer). In one example, a gene expression profile in a subject is read on an array (such as a nucleic acid or protein array). For example, a gene expression profile can be performed using a commercially available array such as a Human Genome U133 2.0 Plus Microarray from AFFYMETRIX® (Santa Clara, Calif.).

Hemochromatosis: A disease characterized by the excessive storage of iron, particularly in the liver, pancreas and other tissues. Hemochromatosis can either be genetic or result from repeated transfusions.

Hepatocellular carcinoma (HCC): HCC is a primary malignancy of the liver typically occurring in patients with inflammatory livers resulting from viral hepatitis, liver toxins or hepatic cirrhosis (often caused by alcoholism).

HCC-associated molecule: As used herein, a "HCC-associated molecule" is a gene or protein whose expression or activity is altered in HCC tumors relative to a control or reference standard. In the context of the present disclosure, HCC-associated molecules include and in some examples consist essentially of or consist of the SH2D4A, CCDC25, ELP3, DLC1, PROSC, SORBS3, HNRPD, PAQR3, PHF17 and DCK genes, or the proteins encoded by these genes. Accordingly, "HCC-associated genes" refers to SH2D4A, CCDC25, ELP3, DLC1, PROSC, SORBS3, HNRPD, PAQR3, PHF17 and DCK and "HCC-associated proteins" refers to the proteins encoded by SH2D4A, CCDC25, ELP3, DLC1, PROSC, SORBS3, HNRPD, PAQR3, PHF17 and DCK. As used herein, "HCC-associated genes" are also referred to as "tumor-associated genes."

Heterogeneous nuclear ribonucleoprotein D (HNRPD): This gene belongs to the subfamily of ubiquitously expressed heterogeneous nuclear ribonucleoproteins (hnRNPs). The hnRNPs are nucleic acid binding proteins that complex with heterogeneous nuclear RNA (hnRNA). These proteins are associated with pre-mRNAs in the nucleus and appear to influence pre-mRNA processing and other aspects of mRNA metabolism and transport. While all of the hnRNPs are present in the nucleus, some seem to shuttle between the nucleus and the cytoplasm. The hnRNP proteins have distinct nucleic acid binding properties. The HNRPD protein has two repeats of quasi-RRM domains that bind to RNAs. HNRPD localizes to both the nucleus and the cytoplasm and is implicated in the regulation of mRNA stability. Alternative splicing of this gene results in four transcript variants. HNRPD is also known as ARE-binding protein AUFI, type A; AU-rich element RNA-binding protein 1; P37; AUF1; AUF1A; HNRNPD; and hnRNPD0. In particular examples, a decrease in expression of HNRPD in HCC or breast cancer, relative to a control, indicates a good prognosis for the HCC or breast cancer patient. The term "HNRPD" includes a HNRPD gene, cDNA, mRNA, or protein.

HNRPD sequences are publically available. For example, GenBank Accession No. AC124016 (deposited Sep. 7, 2002) discloses a human HNRPD gene sequence. GenBank Accession Nos. NM_031370.2 (deposited Aug. 20, 2004) and NP_112738.1 (deposited May 16, 2001) disclose human HNRPD isoform a mRNA and protein sequences, respectively. GenBank Accession Nos. NM_031369.2 and NP_112737.1 (each deposited May 16, 2001) disclose human HNRPD isoform b mRNA and protein sequences, respectively. GenBank Accession Nos. NM_002138.3 and NP_002129.2 (each deposited May 16, 2001) disclose human HNRPD isoform c mRNA and protein sequences, respectively. GenBank Accession Nos. NM_001003810.1 and NP_001003810.1 (each deposited Aug. 20, 2004) disclose human HNRPD isoform d mRNA and protein sequences, respectively. One skilled in the art will appreciate that HNRPD nucleic acid and protein molecules can vary from those publicly available, while still retaining HNRPD biological activity (e.g., decreased expression correlates with a good prognosis for a solid tumor patient).

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each High Stringency (Detects Sequences that Share at Least 80% Identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each Low Stringency (Detects Sequences that Share at Least 60% Identity)
Hybridization: 6×SSC at RT to 55° C. for 16-20 hours
Wash at least twice: 2×-3×SSC at RT to 55° C. for 20-30 minutes each.

Inhibitor: Any chemical compound, nucleic acid molecule or peptide (such as an antibody), specific for a nucleic acid molecule or gene product that can reduce activity of the gene product or directly interfere with expression of a gene (such as an HCC-associated molecule). An inhibitor of the disclosure, for example, can inhibit the activity of a protein that is encoded by the gene either directly or indirectly. Direct inhibition can be accomplished, for example, by binding to a protein and thereby preventing the protein from binding an intended target, such as a receptor. Indirect inhibition can be accomplished, for example, by binding to a protein's intended target, such as a receptor or binding partner, thereby blocking or reducing activity of the protein. Furthermore, an inhibitor of the disclosure can inhibit a gene by reducing or inhibiting expression of the gene, inter alia by interfering with gene expression (transcription, processing, translation, post-translational modification), for example, by interfering with the gene's mRNA and blocking translation of the gene product or by post-translational modification of a gene product, or by causing changes in intracellular localization.

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

Label: An agent capable of detection, for example by ELISA, spectrophotometry, flow cytometry, or microscopy. For example, a label can be attached to a nucleic acid molecule or protein, thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In particular examples, a label is conjugated to a binding agent that specifically binds to one or more of the HCC-associated molecules.

Lung cancer: Cancer that forms in tissues of the lung, usually in the cells lining air passages. The two main types are small cell lung cancer and non-small cell lung cancer.

Malignant: Cells that have the properties of anaplasia invasion and metastasis.

Mammal: This term includes both human and non-human mammals. Examples of mammals include, but are not limited to: humans, pigs, cows, goats, cats, dogs, rabbits and mice.

MicroRNA (miRNA, miR): Single-stranded RNA molecules that regulate gene expression. MicroRNAs are generally 21-23 nucleotides in length. MicroRNAs are processed from primary transcripts known as pri-miRNA to short stem-loop structures called precursor (pre)-miRNA and finally to functional, mature microRNA. Mature microRNA molecules are partially complementary to one or more messenger RNA molecules, and their primary function is to down-regulate gene expression. MicroRNAs regulate gene expression through the RNAi pathway.

More aggressive: As used herein, a "more aggressive" form of a HCC or breast cancer tumor is a tumor with a relatively increased risk of metastasis or recurrence (such as following surgical removal of the tumor). A "more aggressive" HCC or breast cancer tumor can also refer to a HCC or breast cancer tumor that confers an increased likelihood of death, or a decrease in the time until death, upon a subject with the tumor. A subject having a "more aggressive" form of a HCC or breast cancer is considered to have a poor prognosis.

Neoplasm: Abnormal growth of cells.

Node-negative or node-positive: Refer to cancer that has spread (node-positive) or has not spread (node-negative) to the lymph nodes. As used herein, a population of cancer patients with "mixed node status" refers to a group of patients in which some patients are node-negative and some patients are node-positive.

Normal cell: Non-tumor cell, non-malignant, uninfected cell.

Nucleic acid array: An arrangement of nucleic acids (such as DNA or RNA) in assigned locations on a matrix, such as that found in cDNA arrays, or oligonucleotide arrays.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide.

Particular oligonucleotides and oligonucleotide analogs can include linear sequences up to about 200 nucleotides in length, for example a sequence (such as DNA or RNA) that is at least 6 nucleotides, for example at least 8, at least 10, at least 15, at least 20, at least 21, at least 25, at least 30, at least 35, at least 40, at least 45, at least 50, at least 100 or even at least 200 nucleotides long, or from about 6 to about 50 nucleotides, for example about 10-25 nucleotides, such as 12, 15 or 20 nucleotides. In one example, an oligonucleotide is a short sequence of nucleotides of at least one of the disclosed HCC-associated genes, such as SH2D4A, CCDC25, ELP3, DLC1, PROSC, SORBS3, HNRPD, PAQR3, PHF17 or DCK.

Oligonucleotide probe: A short sequence of nucleotides, such as at least 8, at least 10, at least 15, at least 20, at least 21, at least 25, or at least 30 nucleotides in length, used to detect the presence of a complementary sequence by molecular hybridization. In particular examples, oligonucleotide probes include a label that permits detection of oligonucleotide probe:target sequence hybridization complexes. In one example, an oligonucleotide probe is a short sequence of nucleotides used to detect the presence of at least one of the disclosed HCC-associated genes, such as SH2D4A, CCDC25, ELP3, DLC1, PROSC, SORBS3, HNRPD, PAQR3, PHF17 or DCK.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic agents, such as one or more compositions that include a binding agent that specifically binds to at least one of SH2D4A, CCDC25, ELP3, DLC1, PROSC, SORBS3, HNRPD, PAQR3, PHF17 and DCK.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

PHD finger protein 17 (PHF17): A transcriptional co-activator that promotes acetylation of nucleosomal histone H4. PHF17 promotes apoptosis and is thought to function as a renal tumor suppressor. PHF17 also is a protein binding partner of the von Hippel-Lindau tumor suppressor pVHL. PHF17 is also known as Jade-1, FLJ22479 and KIAA1807. In particular examples, a decrease in expression of PHF17 in HCC, relative to a control, indicates a good prognosis for the HCC or breast cancer patient. The term "PHF17" includes a PHF17 gene, cDNA, mRNA, or protein.

PHF17 sequences are publically available. For example, GenBank Accession No. AC093783 (deposited Oct. 20, 2001) discloses a human PHF17 gene sequence. GenBank Accession Nos. NM_024900.3 (deposited Aug. 4, 2006) and NP_079176.2 (deposited Apr. 4, 2002) disclose the short isoform of human PHF17 mRNA and protein sequences, respectively. GenBank Accession Nos. NM_199320.2 (deposited Aug. 4, 2006) and NP_955352.1 (deposited Jan. 4, 2002) disclose the long isoform of human PHF17 mRNA and protein sequences, respectively. One skilled in the art will appreciate that PHF17 nucleic acid and protein molecules can vary from those publicly available, while still retaining PHF17 biological activity (e.g., decreased expression correlates with a good prognosis for a solid tumor patient).

Polymerase chain reaction (PCR): An in vitro amplification technique that increases the number of copies of a nucleic acid molecule (for example, a nucleic acid molecule in a sample or specimen). In an example, a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of a PCR can be characterized by electrophoresis, restriction endonuclease cleavage patterns, oligonucleotide hybridization or ligation, and/or nucleic acid sequencing, using standard techniques or other standard techniques known in the art.

Primers: Short nucleic acid molecules, for instance DNA oligonucleotides 10 to 100 nucleotides in length, such as about 15, 20, 25, 30 or 50 nucleotides or more in length. Primers can be annealed to a complementary target DNA strand by nucleic acid hybridization to form a hybrid between the primer and the target DNA strand. Primer pairs can be used for amplification of a nucleic acid sequence, such as by PCR or other nucleic acid amplification methods known in the art.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length. Thus, in order to obtain greater specificity, primers can be selected that include at least 20, at least 25, at least 30, at least 35, at least 40, at least 45, at least 50 or more consecutive nucleotides of target nucleic acid sequence (such as a HCC-associated molecule).

Progestin and AdipoQ Receptor Family Member III (PAQR3):

A seven-transmembrane domain protein localized to the Golgi apparatus. PAQR3, also known as Raf kinase trapping to Golgi (RKTG), is a negative regulator of the Ras-Raf-mitogen-activated and extracellular signal-regulated kinase kinase (MEKK)-extracellular signal-regulated kinase (ERK)-signaling pathway. In particular examples, a decrease in expression of PAQR3 in HCC or breast cancer, relative to a control, indicates a good prognosis for the HCC or breast cancer patient. The term "PAQR3" includes a PAQR3 gene, cDNA, mRNA, or protein.

PAQR3 sequences are publically available. For example, GenBank Accession No. AC093841 (deposited Feb. 5, 2002) discloses a human PAQR3 gene sequence. GenBank Accession Nos. NM_001040202.1 and NP_001035292.1 (each deposited Apr. 27, 2006) disclose human PAQR3 mRNA and protein sequences, respectively. One skilled in the art will appreciate that PAQR3 nucleic acid and protein molecules can vary from those publicly available, while still retaining PAQR3 biological activity (e.g., decreased expression correlates with a good prognosis for a solid tumor patient).

Prognosis: A prediction of the course of a disease, such as HCC or breast cancer. The prediction can include determining the likelihood of a subject to develop aggressive, recurrent disease, to survive a particular amount of time (e.g. determine the likelihood that a subject will survive 1, 2, 3 or 5 years), to respond to a particular therapy (e.g., chemotherapy), or combinations thereof.

Proline synthetase co-transcribed homolog (PROSC): A protein of unknown function that is ubiquitously expressed in human tissues. PROSC is highly conserved among divergent species from bacteria to mammals, suggesting an important cellular function. The human PROSC cDNA is 2530 base pairs in length and includes 8 exons, encoding a protein of 275 amino acids. PROSC is also known as FLJ11861. In particular examples, an increase in expression of PROSC in HCC or breast cancer, relative to a control, indicates a good prognosis for the HCC or breast cancer patient. The term "PROSC" includes a PROSC gene, cDNA, mRNA, or protein.

PROSC sequences are publically available. For example, GenBank Accession No. AB018566 (deposited Jan. 8, 1999) discloses a human PROSC gene sequence. GenBank Accession Nos. NM_007198.3 (deposited Sep. 16, 2008) and NP_009129.1 (deposited Oct. 1, 1999) disclose human PROSC mRNA and protein sequences, respectively. One skilled in the art will appreciate that PROSC nucleic acid and protein molecules can vary from those publicly available, while still retaining PROSC biological activity (e.g., increased expression correlates with a good prognosis for a solid tumor patient).

Promoter: A sequence sufficient to direct transcription, and which may optionally include additional polynucleotide sequences. In some cases the promoter is a selective promoter capable of rendering promoter-dependent gene expression, for instance which is selective for a specific cell-type, a specific tissue, or a specific time point during development or differentiation. Selective promoters can also be inducible by external signals or agents (that is, "inducing agents"). Selective promoters can modulate anatomical, cell, tissue, temporal and/or spatial expression of a nucleic acid, such as a transgene.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Ribozyme: A catalytic RNA molecule. In some cases, ribozymes can bind to specific sites on other RNA molecules and catalyze the hydrolysis of phosphodiester bonds in the RNA molecules.

RNA interference (RNAi): Refers to a cellular process that inhibits expression of genes, including cellular and viral genes. RNAi is a form of antisense-mediated gene silencing involving the introduction of double stranded RNA-like oligonucleotides leading to the sequence-specific reduction of RNA transcripts. Double-stranded RNA molecules that inhibit gene expression through the RNAi pathway include siRNAs, miRNAs, and shRNAs.

Sample (or biological sample): A biological specimen containing genomic DNA, RNA (including mRNA), protein, or combinations thereof, obtained from a subject. Examples include, but are not limited to, peripheral blood, urine, saliva, tissue biopsy, fine needle aspirate, surgical specimen, and autopsy material. In one example, a sample includes a HCC or breast cancer tissue biopsy.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs may use SEG. In addition, a manual alignment can be performed. Proteins with even greater similarity will show increasing percentage identities when assessed by this method, such as at least about 75%, 80%, 85%, 90%, 95%, 98%, or 99% sequence identity to a native SH2D4A, CCDC25, ELP3, DLC1, PROSC, SORBS3, HNRPD, PAQR3, PHF17 or DCK protein sequence, while retaining the biological function of the protein.

When aligning short peptides (fewer than around 30 amino acids), the alignment is be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, 99% sequence identity to a native SH2D4A, CCDC25, ELP3, DLC1, PROSC, SORBS3, HNRPD, PAQR3, PHF17 or DCK sequence. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity to a native SH2D4A, CCDC25, ELP3, DLC1, PROSC, SORBS3, HNRPD, PAQR3, PHF17 or DCK nucleic acid sequence, and retain the ability to encode a protein with the same biological activity. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside the ranges provided.

SH2 domain containing 4A (SH2D4A): A Src homology 2 (SH2) domain-containing signaling adapter molecule that is expressed in T cells. SH2D4A is also known as SH2A. In particular examples, an increase in expression of SH2D4A in HCC or breast cancer, relative to a control, indicates a good prognosis for the HCC or breast cancer patient. The term "SH2D4A" includes a SH2D4A gene, cDNA, mRNA, or protein.

SH2D4A sequences are publically available. For example, GenBank Accession No. AC068880 (deposited Dec. 11, 2001) discloses a human SH2D4A gene sequence. GenBank Accession Nos. NM_022071.2 and NP_071354.2 (each deposited Jun. 10, 2002) disclose human SH2D4A mRNA and protein sequences, respectively. One skilled in the art will appreciate that SH2D4A nucleic acid and protein molecules can vary from those publicly available, while still retaining SH2D4A biological activity (e.g., increased expression correlates with a good prognosis for a solid tumor patient).

Short hairpin RNA (shRNA): A sequence of RNA that makes a tight hairpin turn and can be used to silence gene expression via the RNAi pathway. The shRNA hairpin structure is cleaved by the cellular machinery into siRNA.

Short interfering RNA (siRNA): A double-stranded nucleic acid molecule that modulates gene expression through the RNAi pathway (See, for example, Bass *Nature* 411:428-9, 2001; Elbashir et al., *Nature* 411:494-8, 2001; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914.). siRNA molecules are generally 20-25 nucleotides in length with 2-nucleotide overhangs on each 3' end. However, siRNAs can also be blunt ended. Generally, one strand of a siRNA molecule is at least partially complementary to a target nucleic acid, such as a target mRNA. siRNAs are also referred to as "small inhibitory RNAs." As used herein, siRNA molecules need not be limited to those molecules containing only RNA, but further encompasses chemically modified nucleotides and non-nucleotides having RNAi capacity or activity. In an example, a siRNA molecule is one that reduces or inhibits the biological activity or expression of HNRPD, PAQR3, PHF17 or DCK. In some examples, commercially available kits, such as siRNA molecule synthesizing kits from PROMEGA® (Madison, Wis.) or AMBION® (Austin, Tex.) may be used to synthesize siRNA molecules. In other examples, siRNAs are obtained from commercial sources, such as from QIAGEN® Inc. (Germantown, Md.), INVITROGEN® (Carlsbad, Calif.), AMBION (Austin, Tex.), DHARMACON® (Lafayette, Colo.), SIGMA-ALDRICH® (Saint Louis, Mo.) or OPENBIOSYSTEMS® (Huntsville, Ala.).

Small molecule: A molecule, typically with a molecular weight less than about 1000 Daltons, or in some embodiments, less than about 500 Daltons, wherein the molecule is capable of modulating, to some measurable extent, an activity of a target molecule.

Solid tumor: An abnormal mass of tissue that usually does not contain cysts or liquid areas. Solid tumors can be either benign (not cancer), or malignant (cancer). Different types of solid tumors are named for the type of cells that form them. Examples of solid tumors include, but are not limited to, sarcomas, carcinomas (e.g., HCC and breast cancer) and lymphomas. In some embodiments, the solid tumor is a HCC, breast cancer, lung cancer, esophageal cancer or colon cancer tumor.

Sorbin and SH3 domain containing 3 (SORBS3): A vinculin-binding cytoskeletal protein involved in focal adhesion and cell-cell adhesion. SORBS3 is also known as SH3D4, SH3-containing adaptor molecule-1 (SCAM-1 or SCAM1) and vinexin. In particular examples, an increase in expression of SORBS3 in HCC or breast cancer, relative to a control, indicates a good prognosis for the HCC or breast cancer patient. The term "SORBS3" includes a SORBS3 gene, cDNA, mRNA, or protein.

SORBS3 sequences are publically available. For example, GenBank Accession No. AC037459 (deposited Dec. 18, 2002) discloses a human SORBS3 gene sequence. GenBank Accession Nos. NM_005775 and NP_005766 (each deposited Aug. 10, 2007) disclose human SORBS3 isoform 1 mRNA and protein sequences, respectively. In addition, GenBank Accession No. NM_001018003 (deposited Aug. 10, 2007) discloses the human SORBS3 isoform 2 mRNA and protein sequences. One skilled in the art will appreciate that SORBS3 nucleic acid and protein molecules can vary from those publicly available, while still retaining SORBS3 biological activity (e.g., increased expression correlates with a good prognosis for a solid tumor patient).

Specific binding agent: An agent that binds substantially or preferentially only to a defined target such as a protein, enzyme, polysaccharide, oligonucleotide, DNA, RNA, recombinant vector or a small molecule. In an example, a "specific binding agent" is capable of binding to at least one of SH2D4A, CCDC25, ELP3, DLC1, PROSC, SORBS3, HNRPD, PAQR3, PHF17 and DCK. In other examples, the specific binding agent is capable of binding to a downstream factor regulated by SH2D4A, CCDC25, ELP3, DLC1, PROSC, SORBS3, HNRPD, PAQR3, PHF17 or DCK. Thus, a nucleic acid-specific binding agent binds substantially only to the defined nucleic acid, such as RNA, or to a specific region within the nucleic acid. For example, a "specific binding agent" includes an antisense compound (such as an antisense oligonucleotide, siRNA, miRNA, shRNA or ribozyme) that binds substantially to a specified RNA.

A protein-specific binding agent binds substantially only the defined protein, or to a specific region within the protein. For example, a "specific binding agent" includes antibodies and other agents that bind substantially to a specified polypeptide. Antibodies include monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Subject: Living multi-cellular vertebrate organisms, a category that includes human and non-human mammals.

Target sequence: A sequence of nucleotides located in a particular region in the human genome that corresponds to a desired sequence, such as a HCC-associated gene, for example, SH2D4A, CCDC25, ELP3, DLC1, PROSC, SORBS3, HNRPD, PAQR3, PHF17 or DCK. Target sequences can encode target proteins. The target can be for instance a coding sequence; it can also be the non-coding strand that corresponds to a coding sequence. Examples of target sequences include those sequences associated with HCC or breast cancer.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject. For example, therapeutic agents for HCC or breast cancer include agents that prevent or inhibit development or metastasis of HCC or breast cancer, respectively. As used herein, a "candidate agent" is a compound selected for screening to determine if it can function as a therapeutic agent for HCC or breast cancer. In some embodiments, the candidate agent is identified as a therapeutic agent if the agent increases expression of a HCC-associated gene, such as SH2D4A, CCDC25, ELP3, DLC1, PROSC or SORBS3, or a protein encoded thereby. In some embodiments, the candidate agent is identified as a therapeutic agent if the agent decreases expression of a HCC-associated gene, such as HNRPD, PAQR3, PHF17 or DCK, or a protein encoded thereby. "Incubating" includes a sufficient amount of time for an agent to interact with a cell or tissue. "Contacting" includes incubating an agent in solid or in liquid form with a cell or tissue. "Treating" a cell or tissue with an agent includes contacting or incubating the agent with the cell or tissue.

Therapeutically effective amount: An amount of a composition that alone, or together with an additional therapeutic agent(s) (for example a chemotherapeutic agent), induces the desired response (e.g., treatment of a tumor). The preparations disclosed herein are administered in therapeutically effective amounts. In one example, a desired response is to decrease tumor size or volume or metastasis in a subject to whom the therapy is administered. The tumor or metastasis thereof does not need to be completely eliminated for the composition to be effective. For example, a composition can decrease the size or volume of a tumor or the metastasis of the tumor by a desired amount, for example by at least 20%, at least 50%, at least 60%, at least 70%, at least 80%, at least 90%, at least 95%, at least 98%, or even at least 100% (elimination of the tumor), as compared to the size or volume of the tumor or metastasis in the absence of the composition.

In particular examples, it is an amount of the therapeutic agent effective to decrease the number of tumor cells, such as the number of tumor cells in a patient with HCC or breast cancer. The tumor cells do not need to be completely eliminated for the composition to be effective. For example, a composition can decrease the number of tumor cells by a desired amount, for example by at least 20%, at least 50%, at least 60%, at least 70%, at least 80%, at least 90%, at least 95%, at least 98%, or even at least 100% (elimination of detectable tumor cells), as compared to the number of tumor cells in the absence of the composition.

A therapeutically effective amount of a specific binding agent for at least one of the disclosed HCC-associated molecules can be administered in a single dose, or in several doses, for example daily, during a course of treatment. However, the therapeutically effective amount can depend on the subject being treated, the severity and type of the condition being treated, the manner of administration and the type of therapeutic agent being administered. For example, a therapeutically effective amount of such agent can vary from about 1 µg-10 mg per 70 kg body weight if administered intravenously and about 10 µg-100 mg per 70 kg body weight if administered intratumorally.

Tissue: A plurality of functionally related cells. A tissue can be a suspension, a semi-solid, or solid. Tissue includes cells collected from a subject, such as the liver, breast or lymph node.

Treating a disease: "Treatment" refers to a therapeutic intervention that ameliorates a sign or symptom of a disease or pathological condition, such as a sign or symptom of HCC or breast cancer. Treatment can also induce remission or cure of a condition, such as HCC or breast cancer. In particular examples, treatment includes preventing a disease, for example by inhibiting the full development of a disease or metastasis of a tumor. Prevention of a disease does not require a total absence of disease. For example, a decrease of at least 50% can be sufficient. In some examples, treating a disease improves the prognosis of the HCC or breast cancer patient, for example by increasing the predicted survival time of the HCC or breast cancer patient.

Tumor: All neoplastic cell growth and proliferation, whether malignant or benign, and all pre-cancerous and cancerous cells and tissues. In an example, a tumor is a HCC tumor or breast cancer.

Tumor-associated molecule: As used herein, a "tumor-associated molecule" is a gene or protein whose expression or activity is altered in solid tumors (such as HCC or breast cancer) relative to a control or reference standard. In the context of the present disclosure, tumor-associated molecules include the SH2D4A, CCDC25, ELP3, DLC1, PROSC, SORBS3, HNRPD, PAQR3, PHF17 and DCK genes, or the proteins encoded by these genes. Accordingly, "tumor-associated genes" refers to SH2D4A, CCDC25, ELP3, DLC1, PROSC, SORBS3, HNRPD, PAQR3, PHF17 and DCK and "tumor-associated proteins" refers to the proteins encoded by SH2D4A, CCDC25, ELP3, DLC1, PROSC, SORBS3, HNRPD, PAQR3, PHF17 and DCK. As used herein, "tumor-associated genes" are also referred to as "HCC-associated genes."

Tumor-Node-Metastasis (TNM): The TNM classification of malignant tumors is a cancer staging system for describing the extent of cancer in a patient's body. T describes the size of the primary tumor and whether it has invaded nearby tissue; N describes any lymph nodes that are involved; and M describes metastasis. TNM is developed and maintained by the International Union Against Cancer to achieve consensus on one globally recognized standard for classifying the extent of spread of cancer. The TNM classification is also used by the American Joint Committee on Cancer and the International Federation of Gynecology and Obstetrics.

Under conditions sufficient for: A phrase that is used to describe any environment that permits the desired activity. In one example, includes administering a test agent to a HCC cell or a subject sufficient to allow the desired activity. In particular examples, the desired activity is altering the activity (such as the expression) of SH2D4A, CCDC25, ELP3, DLC1, PROSC, SORBS3, HNRPD, PAQR3, PHF17 or DCK.

Unit dose: A physically discrete unit containing a predetermined quantity of an active material calculated to individually or collectively produce a desired effect, such as a therapeutic effect. A single unit dose or a plurality of unit doses can be used to provide the desired effect, such as treatment of HCC or breast cancer, for example a metastatic tumor. In one example, a unit dose includes a desired amount of an agent that decreases or inhibits metastasis. In a particular example, a unit dose includes a desired amount of an agent that increases or upregulates expression of a molecule that is undesirably downregulated in HCC or breast cancer (such as SH2D4A, CCDC25, ELP3, DLC1, PROSC and/or SORBS3).

Upregulated, activated or increased: When used in reference to the expression of a nucleic acid molecule, such as a gene, refers to any process which results in an increase in production of a gene product. A gene product can be RNA (such as mRNA, rRNA, tRNA, and structural RNA) or protein. Therefore, gene upregulation or activation includes processes that increase transcription of a gene or translation of mRNA.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene upregulation can include inhibition of repression as well as stimulation of expression above an existing level. Examples of processes that increase translation include those that increase translational initiation, those that increase translational elongation and those that increase mRNA stability.

Gene upregulation includes any detectable increase in the production of a gene product. In certain examples, production of a gene product (such as SH2D4A, CCDC25, ELP3, DLC1, PROSC, SORBS3, HNRPD, PAQR3, PHF17 or DCK) increases by at least 2-fold, for example at least 3-fold or at least 4-fold, as compared to a control (such an amount of gene expression in a normal cell). In one example, a control is a relative amount of gene expression in a biological sample, such as in a liver tissue biopsy obtained from a subject that does not have HCC.

Vector: A nucleic acid molecule that can be introduced into a host cell. A vector can include nucleic acid sequences that permit it to replicate in the host cell, such as an origin of replication. A vector can also include one or more selectable marker genes and other genetic elements. An insertional vector is capable of inserting itself into a host nucleic acid. In some embodiments herein, a vector is a non-viral vector, such as a plasmid. In other embodiments, the vector is a viral vector, such as an adenovirus vector, an adeno-associated virus vector, a lentivirus vector, a retrovirus vector or a herpesvirus vector.

Additional terms commonly used in molecular genetics can be found in Benjamin Lewin, Genes V published by Oxford University Press, 1994 (ISBN 0-19-854287-9); Kendrew et al (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All GenBank Accession Nos. mentioned herein are incorporated by reference in their entirety. In case of conflict, the present specification, including explanations of terms, will control. In addition, the materials, methods, and examples are illustrative only and not intended to be limiting.

IV. Driver Gene Signature

Described herein is the identification of a driver gene signature for the prediction of clinical outcome of patients diagnosed with solid tumors. In some embodiments, the solid tumor is an HCC, breast cancer, lung cancer, esophageal cancer or colon cancer tumor. In particular examples, the solid tumor is an HCC tumor or breast cancer tumor. The ten-gene signature includes SH2D4A, CCDC25, ELP3, DLC1, PROSC, SORBS3, HNRPD, PAQR3, PHF17 and DCK, each of which is encoded in a loss region of chromosome 4q or chromosome 8p in tumor samples from HCC patients. Correlation analysis of gene expression and DNA copy number led to the identification of the ten driver gene signature. The six genes located in loss regions of chromosome 8p (SH2D4A, CCDC25, ELP3, DLC1, PROSC and SORBS3) are associated with poor coutcome, while the four genes located in loss regions of chromosome 4q (HNRPD, PAQR3, PHF17 and DCK) are associated with good prognosis.

Thus, provided herein is a method of predicting the prognosis of a subject diagnosed with HCC. The method includes detecting expression of two or more HCC-associated genes, wherein the HCC-associated genes include SH2D4A, CCDC25, ELP3, DLC1, PROSC, SORBS3, HNRPD, PAQR3, PHF17 and DCK, and comparing expression of the HCC-associated genes in the tumor sample to a control. Also provided herein is a method of predicting the prognosis of a subject diagnosed with breast cancer. The method includes detecting expression of two or more tumor-associated genes, wherein the tumor-associated genes include SH2D4A, CCDC25, ELP3, DLC1, PROSC, SORBS3, HNRPD, PAQR3, PHF17 and DCK, and comparing expression of the tumor-associated genes in the tumor sample to a control. Further provided is a method of predicting the prognosis of a subject diagnosed with other types of solid tumors, including lung cancer, esophageal cancer or colon cancer. The method includes detecting expression of two or more tumor-associated genes, wherein the tumor-associated genes include SH2D4A, CCDC25, ELP3, DLC1, PROSC, SORBS3, HNRPD, PAQR3, PHF17 and DCK, and comparing expression of the tumor-associated genes in the tumor sample to a control.

In some embodiments, the methods include detecting expression of three or more, four or more, five or more, six or more, seven or more, eight or more or nine or more HCC-associated genes (or tumor-associated genes). In one example, the method includes detecting expression of a plurality of HCC-associated genes in a tumor sample obtained from the subject, wherein the plurality of HCC-associated genes consists essentially of or consists of SH2D4A, CCDC25, ELP3, DLC1, PROSC, SORBS3, HNRPD, PAQR3, PHF17 and DCK. In some examples, housekeeping gene expression is also detected, such as 1 to 10, 1 to five, or one to two housekeeping genes.

In some embodiments of the method, a decrease in expression of one or more HCC-associated genes (or tumor-associated genes) selected from SH2D4A, CCDC25, ELP3, DLC1, PROSC and SORBS3 in the tumor sample relative to the control indicates a poor prognosis. In some embodiments, an increase in expression of one or more HCC-associated genes selected from HNRPD, PAQR3, PHF17 and DCK in the tumor sample relative to the control indicates a poor prognosis. In particular examples, a decrease in expression of two or more, three or more, four or more, five or more, or each of SH2D4A, CCDC25, ELP3, DLC1, PROSC and SORBS3 in the tumor sample relative to the control indicates a poor prognosis. In some examples, an increase in expression of two or more, three or more, or each of HNRPD, PAQR3, PHF17 and DCK in the tumor sample relative to the control indicates a poor prognosis. In some embodiments, a poor prognosis is indicated by a decrease in expression of one or more of SH2D4A, CCDC25, ELP3, DLC1, PROSC and SORBS3, and an increase in expression of one or more HNRPD, PAQR3, PHF17 and DCK, including any combinations thereof. For example, expression of at least two, at least three, at least four, at least five, at least six, at least seven, at least eight, at least nine or all ten genes can be altered.

Expression of the HCC-associated genes (or tumor-associated genes) can be detected using any suitable means known in the art. For example, detection of gene expression can be accomplished using RT-PCR or array analysis. Additional methods of detecting gene expression are well known in the art and are described in greater detail below.

The increase or decrease in expression of the HCC-associated genes (or tumor-associated genes) can be any measurable increase or decrease in expression that is correlated with a poor prognosis. In some embodiments, the increase or decrease in expression is about 1.5-fold, about 2-fold, about 2.5-fold, about 3-fold, about 4-fold, about 5-fold, about 7-fold or about 10-fold. The relative increase or decrease in expression level amongst the HCC-associated genes can vary within a tumor and can also vary between tumor samples.

In an alternative embodiment, prognosis of the HCC or breast cancer patient is determined or predicted by detecting DNA copy number of one or more of the disclosed HCC-associated genes (also referred to as "tumor-associated genes) in a tumor sample. For example, genomic DNA can be amplified, such as by PCR, to detect the presence or absence of gene deletions of one or more of SH2D4A, CCDC25, ELP3, DLC1, PROSC, SORBS3, HNRPD, PAQR3, PHF17 and DCK. A reduction in DNA copy number of one or more of SH2D4A, CCDC25, ELP3, DLC1, PROSC, SORBS3, and/or an increase in DNA copy number of one or more of HNRPD, PAQR3, PHF17 and DCK in a tumor sample, relative to a control, indicates a poor prognosis for the HCC or breast cancer patient.

Poor prognosis can refer to any negative clinical outcome, such as, but not limited to, a decrease in likelihood of survival, a decrease in the time of survival (e.g., less than 5 years, or less than one year), an increase in the severity of disease, a decrease in response to therapy, an increase in tumor recurrence, an increase in metastasis, or the like.

The control can be any suitable control against which to compare expression of a HCC-associated gene in a tumor sample. In some embodiments, the control sample is non-tumor tissue. In some examples, the non-tumor tissue is obtained from the same subject, such as non-tumor liver tissue that is adjacent to the HCC tumor (or non-tumor breast tissue that is adjacent to the breast tumor). In other examples, the non-tumor tissue is obtained from a healthy control subject (such as a subject who has not had and does not have cancer). In some embodiments, the control is a reference value. For example, the reference value can be derived from the average expression values obtained from a group of healthy control subjects or non-tumor tissue from a group of HCC or breast cancer patients.

The methods described herein can be used to predict the prognosis of a HCC patient with any type of disease etiology. In some embodiments, the subject diagnosed with HCC has a chronic viral infection. In one example, the chronic infection is a hepatitis B virus infection. In another example, the chronic infection is a hepatitis C virus infection. In other embodiments, the subject diagnosed with HCC has cirrhosis of the liver. In one example, cirrhosis of the liver is caused by chronic alcohol consumption. In another example, cirrhosis of the liver is caused by inherited hemochromatosis. In another example, cirrhosis of the liver is caused by exposure to aflatoxin, such as by ingestion of aflatoxin-contaminated food.

In some embodiments of the method for predicting the prognosis of a breast cancer patient, the patient is node-positive (i.e., the breast cancer has spread to the lymph nodes).

V. Detecting Expression of HCC-Associated Genes

As described below, expression of one or more HCC-associated genes (also referred to herein as "tumor-associated genes") can be detected using any one of a number of methods well known in the art. Expression of either mRNA or protein is contemplated herein.

A. Methods for Detection of mRNA

Gene expression can be evaluated by detecting mRNA encoding the gene of interest. Thus, the disclosed methods can include evaluating mRNA encoding SH2D4A, CCDC25, ELP3, DLC1, PROSC, SORBS3, HNRPD, PAQR3, PHF17 or DCK. In some examples, the mRNA is quantified.

RNA can be isolated from a sample of a solid tumor (such as a HCC tumor or breast cancer tumor) from a subject, a sample of adjacent non-tumor tissue from the subject, from tumor-free tissue from a normal (healthy) subject, or combinations thereof, using methods well known to one skilled in the art, including commercially available kits. General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., *BioTechniques* 18:42044 (1995). In one example, RNA isolation can be performed using purification kit, buffer set and protease from commercial manufacturers, such as QIAGEN®, according to the manufacturer's instructions. For example, total RNA from cells in culture (such as those obtained from a subject) can be isolated using QIAGIN® RNeasy mini-columns. Other commercially available RNA isolation kits include MASTERPURE®. Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared from tumor or other biological sample can be isolated, for example, by cesium chloride density gradient centrifugation.

Methods of gene expression profiling include methods based on hybridization analysis of polynucleotides, methods based on sequencing of polynucleotides, and proteomics-based methods. In some examples, mRNA expression in a sample is quantified using northern blotting or in situ hybridization (Parker & Barnes, Methods in Molecular Biology 106:247-283, 1999); RNAse protection assays (Hod, *Biotechniques* 13:852-4, 1992); and PCR-based methods, such as reverse transcription polymerase chain reaction (RT-PCR) (Weis et al., *Trends in Genetics* 8:263-4, 1992). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). In one example, RT-PCR can be used to compare mRNA levels in different samples, in normal and tumor tissues, with or without drug treatment, to characterize patterns of gene expression, to discriminate between closely related mRNAs, and to analyze RNA structure.

Methods for quantifying mRNA are well known in the art. In some examples, the method utilizes RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN® RT-PCR can be performed using commercially available equipment, such as, for example, ABI PRISM 7700® Sequence Detection System® (Perkin-Elmer-Applied Biosystems, Foster City, Calif.), or Lightcycler (Roche Molecular Biochemicals, Mannheim, Germany). In one example, the 5' nuclease procedure is run on a real-time quantitative PCR device such as the ABI PRISM 7700® Sequence Detection System®. The system includes of thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by the experimental treatment. RNAs commonly used to normalize patterns of gene expression are mRNAs for the housekeeping genes glyceraldehyde-3-phosphate-dehydrogenase (GAPDH), beta-actin, and 18S ribosomal RNA.

A variation of RT-PCR is real time quantitative RT-PCR, which measures PCR product accumulation through a dual-labeled fluorogenic probe (e.g., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Held et al., *Genome Research* 6:986 994, 1996). Quantitative PCR is also described in U.S. Pat. No. 5,538,848. Related probes and quantitative amplification procedures are described in U.S. Pat. No. 5,716,784 and U.S. Pat. No. 5,723,591. Instruments for carrying out quantitative PCR in microtiter plates are available from PE Applied Biosystems, 850 Lincoln Centre Drive, Foster City, Calif. 94404 under the trademark ABI PRISM® 7700.

The steps of a representative protocol for quantifying gene expression using fixed, paraffin-embedded tissues as the RNA source, including mRNA isolation, purification, primer extension and amplification are given in various publications (see Godfrey et al., *J. Mol. Diag.* 2:84 91, 2000; Specht et al., *Am. J. Pathol.* 158:419-29, 2001). Briefly, a representative process starts with cutting about 10 µm thick sections of paraffin-embedded tumor tissue samples or adjacent non-cancerous tissue. The RNA is then extracted, and protein and DNA are removed. Alternatively, RNA is located directly from a tumor sample or other tissue sample. After analysis of the RNA concentration, RNA repair and/or amplification steps can be included, if necessary, and RNA is reverse transcribed using gene specific promoters followed by RT-PCR. The primers used for the amplification are selected so as to amplify a unique segment of the gene of interest, such as mRNA encoding SH2D4A, CCDC25, ELP3, DLC1, PROSC, SORBS3, HNRPD, PAQR3, PHF17 and DCK. In some embodiments, expression of other genes is also detected. Primers that can be used to amplify SH2D4A, CCDC25, ELP3, DLC1, PROSC, SORBS3, HNRPD, PAQR3, PHF17 and DCK are commercially available or can be designed and synthesized according to well known methods.

An alternative quantitative nucleic acid amplification procedure is described in U.S. Pat. No. 5,219,727. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some embodiments of this method, the expression of a "house keeping" gene or "internal control" can also be evaluated. These terms include any constitutively or globally expressed gene whose presence enables an assessment of HCC-associated gene mRNA levels. Such an assessment includes a determination of the overall constitutive level of gene transcription and a control for variations in RNA recovery.

In some examples, gene expression is identified or confirmed using the microarray technique. Thus, the expression profile can be measured in either fresh or paraffin-embedded tumor tissue, using microarray technology. In this method, HCC-associated gene nucleic acid sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors, and optionally from corresponding noncancerous tissue and normal tissues or cell lines.

In a specific embodiment of the microarray technique, PCR amplified inserts of cDNA clones are applied to a substrate in a dense array. At least probes specific for two or more of SH2D4A, CCDC25, ELP3, DLC1, PROSC, SORBS3, HNRPD, PAQR3, PHF17 and DCK nucleotide sequences are applied to the substrate, and the array can consist essentially of, or consist of these sequences. The microarrayed nucleic acids are suitable for hybridization under stringent conditions. Fluorescently labeled cDNA probes may be generated through incorporation of fluorescent nucleotides by reverse transcription of RNA extracted from tissues of interest.

Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for SH2D4A, CCDC25, ELP3, DLC1, PROSC, SORBS3, HNRPD, PAQR3, PHF17 and DCK. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):10614-9, 1996). Microarray analysis can be performed by commercially available equipment, following manufacturer's protocols, such as are supplied with Affymetrix GenChip technology, or Incyte's microarray technology.

Serial analysis of gene expression (SAGE) is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-7, 1995; and Velculescu et al., *Cell* 88:243-51, 1997, herein incorporated by reference).

In situ hybridization (ISH) is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of HCC-associated genes.

Sample cells or tissues are treated to increase their permeability to allow a probe, such as an HCC-associated gene-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a non-cancerous, breast cancer or HCC tumor sample. Since the sequences of the HCC-associated genes of interest are known, probes can be designed accordingly such that the probes specifically bind the gene of interest.

In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

B. Arrays for Profiling Tumor-Associated Gene Expression

In particular embodiments provided herein, arrays are provided that can be used to evaluate tumor-associated gene expression, for example to prognose a patient with HCC or breast cancer. When describing an array that consists essentially of probes or primers specific for SH2D4A, CCDC25, ELP3, DLC1, PROSC, SORBS3, HNRPD, PAQR3, PHF17 and DCK, such an array includes probes or primers specific for these 10 tumor-associated genes, and can further include control probes (for example to confirm the incubation conditions are sufficient). In some examples, the array may further comprise additional, such as 1, 2, 3, 4 or 5 additional tumor-associated genes. In other examples, the array may include fewer, such as 1, 2, 3, 4 or 5 fewer tumor-associated genes. Exemplary control probes include GAPDH, actin, and YWHAZ. In one example, an array is a multi-well plate (e.g., 98 or 364 well plate).

In one example, the array includes, consists essentially of, or consists of probes or primers (such as an oligonucleotide or antibody) that can recognize SH2D4A, CCDC25, ELP3, DLC1, PROSC, SORBS3, HNRPD, PAQR3, PHF17 and/or DCK. The oligonucleotide probes or primers can further include one or more detectable labels, to permit detection of hybridization signals between the probe and target sequence (such as one of the 10 tumor-associated genes disclosed herein).

i. Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoride, polyfluoroethylene-propylene, polyethylenevinyl alcohol, polymethylpentene, polycholorotrifluoroethylene, polysulformes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides or proteins (such as antibodies) are not amenable to non-specific binding, or when non-specific binding occurs, such materials can be readily removed from the surface without removing the oligonucleotides or proteins (such as antibodies).

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

ii. Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit a low background fluorescence.

The array formats of the present disclosure can be included in a variety of different types of formats. A "format" includes any format to which the solid support can be affixed, such as microtiter plates (e.g., multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217: 306-10, 1994. In one example, the oligonucleotides are synthesized onto the support using conventional chemical techniques for preparing oligonucleotides on solid supports (such as see PCT applications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

C. Methods for Detection of Protein

In some examples, expression of SH2D4A, CCDC25, ELP3, DLC1, PROSC, SORBS3, HNRPD, PAQR3, PHF17 and DCK proteins is analyzed. Suitable biological samples include samples containing protein obtained from a solid tumor of a subject (such as a HCC or breast tumor of a subject), non-tumor tissue from the subject, and/or protein obtained from one or more samples of cancer-free subjects. An alteration in the amount of SH2D4A, CCDC25, ELP3, DLC1, PROSC, SORBS3, HNRPD, PAQR3, PHF17 and DCK proteins in a tumor from the subject relative to a control, such as an increase or decrease in expression, indicates the prognosis of the subject, as described above.

Antibodies specific for SH2D4A, CCDC25, ELP3, DLC1, PROSC, SORBS3, HNRPD, PAQR3, PHF17 and DCK proteins can be used for detection and quantification of tumor-associated proteins by one of a number of immunoassay methods that are well known in the art, such as those presented in Harlow and Lane (Antibodies, A Laboratory Manual, CSHL, New York, 1988). Methods of constructing such antibodies are known in the art.

Any standard immunoassay format (such as ELISA, Western blot, or RIA assay) can be used to measure protein levels. Thus, SH2D4A, CCDC25, ELP3, DLC1, PROSC, SORBS3, HNRPD, PAQR3, PHF17 and DCK polypeptide levels in a tumor can readily be evaluated using these methods. Immunohistochemical techniques can also be utilized for tumor-associated gene detection and quantification. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantifying tumor-associated proteins, a biological sample of the subject that includes cellular proteins can be used. Quantification of SH2D4A, CCDC25, ELP3, DLC1, PROSC, SORBS3, HNRPD, PAQR3, PHF17 and DCK protein can be achieved by immunoassay methods known in the art. The amount SH2D4A, CCDC25, ELP3, DLC1, PROSC, SORBS3, HNRPD, PAQR3, PHF17 and DCK protein can be assessed in the tumor and optionally in the adjacent non-tumor tissue or in tissue from cancer-free subjects. The amounts of SH2D4A, CCDC25, ELP3, DLC1, PROSC, SORBS3, HNRPD, PAQR3, PHF17 and DCK protein in the tumor can be compared to levels of the protein found in cells from a cancer-free subject or other control (such as a standard value or reference value). A significant increase or decrease in the amount can be evaluated using statistical methods disclosed herein and/or known in the art.

Quantitative spectroscopic approaches methods, such as SELDI, can be used to analyze SH2D4A, CCDC25, ELP3, DLC1, PROSC, SORBS3, HNRPD, PAQR3, PHF17 and DCK expression in a sample (such as non-cancerous tissue, tumor tissue, and tissue from a cancer-free subject). In one example, surface-enhanced laser desorption-ionization time-of-flight (SELDI-TOF) mass spectrometry is used to detect protein expression, for example by using the ProteinChip™ (Ciphergen Biosystems, Palo Alto, Calif.). Such methods are well known in the art (for example see U.S. Pat. No. 5,719, 060; U.S. Pat. No. 6,897,072; and U.S. Pat. No. 6,881,586). SELDI is a solid phase method for desorption in which the analyte is presented to the energy stream on a surface that enhances analyte capture or desorption.

Briefly, one version of SELDI uses a chromatographic surface with a chemistry that selectively captures analytes of interest, such as HCC-associated proteins. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as tumor-associated proteins) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection means can be implemented in series to fully interrogate the analyte components and function associated with retained molecules at each location in the array.

Therefore, in a particular example, the chromatographic surface includes antibodies that specifically bind SH2D4A, CCDC25, ELP3, DLC1, PROSC, SORBS3, HNRPD, PAQR3, PHF17 and DCK. In other examples, the chromatographic surface consists essentially of, or consists of, antibodies that specifically bind SH2D4A, CCDC25, ELP3, DLC1, PROSC, SORBS3, HNRPD, PAQR3, PHF17 and DCK. In some examples, the chromatographic surface includes antibodies that bind other molecules, such as housekeeping proteins (e.g. actin or myosin).

In another example, antibodies are immobilized onto the surface using a bacterial Fc binding support. The chromatographic surface is incubated with a sample, such as a sample of a HCC tumor. The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

D. Method of Detecting Gene Deletions

Methods of detecting the presence or absence of a gene deletion are well known in the art. For example, genomic DNA can be isolated from a subject, such as from a tumor sample or adjacent non-tumor sample and subjected to amplification by PCR using primers specific for genomic sequences of interest. In particular examples, the PCR primers are designed to amplify genomic regions corresponding to one or more tumor-associated genes, such as SH2D4A, CCDC25, ELP3, DLC1, PROSC, SORBS3, HNRPD, PAQR3, PHF17 or DCK. Alternatively, DNA copy number can be assessed using a genomic array-based method, such as described in Example 1 below.

VI. Application of a Gene Signature for Treatment of Solid Tumors

It is disclosed herein that DNA copy number and mRNA expression of SH2D4A, CCDC25, ELP3, DLC1, PROSC, SORBS3, HNRPD, PAQR3, PHF17 and DCK correlate with clinical outcome of HCC and breast cancer patients. In particular, a decrease in DNA copy number or mRNA expression of SH2D4A, CCDC25, ELP3, DLC1, PROSC and SORBS3 in HCC and breast tumors is associated with a poor prognosis, while a decrease in DNA copy number or mRNA expression of HNRPD, PAQR3, PHF17 and DCK in HCC or breast tumors is associated with a good prognosis. As such, an increase in expression or activity of one or more of SH2D4A, CCDC25, ELP3, DLC1, PROSC and SORBS3, or a decrease in expression or activity of one or more of HNRPD, PAQR3, PHF17 and DCK would be beneficial for inhibiting the development or progression of HCC or breast cancer.

A. Methods of Treatment

Provided herein is a method of treating HCC in a subject, including administering to the subject a therapeutically effective amount of an agent that alters expression or activity of at least one HCC-associated molecule, for example, SH2D4A, CCDC25, ELP3, DLC1, PROSC, SORBS3, HNRPD, PAQR3, PHF17 or DCK. Also provided herein is a method of treating breast cancer in a subject, including administering to the subject a therapeutically effective amount of an agent that alters expression or activity of at least one tumor-associated molecule, for example, SH2D4A, CCDC25, ELP3, DLC1, PROSC, SORBS3, HNRPD, PAQR3, PHF17 or DCK. In other embodiments of the method, the patient to be treated is a patient with another type of solid tumor, such as a lung cancer, esophageal cancer or colon cancer tumor.

In particular examples of the methods, the agent increases expression of SH2D4A, CCDC25, ELP3, DLC1, PROSC or SORBS3. In other examples, the agent decreases expression of HNRPD, PAQR3, PHF17 or DCK. Such agents can alter the expression of nucleic acid sequences (such as DNA, cDNA, or mRNAs) or proteins. In other examples, the agent increases the biological activity of SH2D4A, CCDC25, ELP3, DLC1, PROSC or SORBS3, or decreases the biological activity of HNRPD, PAQR3, PHF17 or DCK. In particular examples, the agent increases expression of SH2D4A or SORBS3 (for instance, the agent can be an expression vector encoding SH2D4A and SORBS3). An increase or decrease in the expression or activity can be any detectable increase or decrease that results in a biological effect. For example, an agent can increase or decrease the expression or activity by a desired amount, for example by at least about 1.5-fold, at least about 2-fold, at least about 2.5-fold, at least about 3-fold, at least about 4-fold, at least about 5-fold, at least about 7-fold, or at least about 10-fold relative to activity or expression in a control.

Treatment of a solid tumor, such as HCC or breast cancer, by altering the expression or activity of one or more of SH2D4A, CCDC25, ELP3, DLC1, PROSC, SORBS3, HNRPD, PAQR3, PHF17 and DCK can include delaying the development of the tumor in a subject (such as preventing metastasis of a tumor). Treatment of a solid tumor also includes reducing signs or symptoms associated with the presence of such a tumor (for example by reducing the size or volume of the tumor or a metastasis thereof). Such reduced growth can in some examples decrease or slow metastasis of the tumor, or reduce the size or volume of the tumor by at least 10%, at least 20%, at least 50%, or at least 75%.

In some embodiments, the agent is a specific binding agent, such as an antibody, antisense compound or small molecule inhibitor. Methods of preparing antibodies against a specific target protein are well known in the art. A tumor-associated protein or a fragment or conservative variant thereof can be used to produce antibodies which are immunoreactive or specifically bind to an epitope of the tumor-associated protein. Polyclonal antibodies, antibodies which consist essentially of pooled monoclonal antibodies with different epitopic specificities, as well as distinct monoclonal antibody preparations are included. The preparation of polyclonal antibodies is well known to those skilled in the art. See, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992. The preparation of monoclonal antibodies likewise is conventional (see, for example, Kohler & Milstein, *Nature* 256:495, 1975; Coligan et al., sections 2.5.1-2.6.7; and Harlow et al. in: *Antibodies: a Laboratory Manual*, page 726, Cold Spring Harbor Pub., 1988).

Any type of antisense compound that specifically targets and regulates expression of target nucleic acid (such as an HCC-associated gene or downstream target thereof) is contemplated for use, for example when downregulation or decreased expression of a molecule is desired, such as in the case of HNRPD, PAQR3, PHF17 and DCK. In some examples, the agent is an antisense compound selected from an antisense oligonucleotide, a siRNA, a miRNA, a shRNA or a ribozyme. Methods of designing, preparing and using antisense compounds are within the abilities of one of skill in the art. Furthermore, sequences for the disclosed tumor-associated genes are publicly available. Antisense compounds specifically targeting a tumor-associated gene (or other target nucleic acid) can be prepared by designing compounds that are complementary to the target nucleotide sequence, such as an mRNA sequence. Antisense compounds need not be 100% complementary to the target nucleic acid molecule to specifically hybridize and regulate expression the target gene. For example, the antisense compound, or antisense strand of the compound if a double-stranded compound, can be at least 75%, at least 80%, at least 85%, at least 90%, at least 95%, at least 99% or 100% complementary to the selected target nucleic acid sequence. Methods of screening antisense compounds for specificity are well known in the art (see, for example, U.S. Patent Application Publication No. 2003-0228689).

Also provided is a method of treating HCC in a subject by administering to the subject a therapeutically effective amount of an isolated nucleic acid molecule encoding an HCC-associated gene (or tumor-associated gene) selected from SH2D4A, CCDC25, ELP3, DLC1, PROSC and SORBS3. Similarly, provided herein is a method of treating breast cancer in a subject by administering to the subject a therapeutically effective amount of an isolated nucleic acid molecule encoding a tumor-associated gene selected from SH2D4A, CCDC25, ELP3, DLC1, PROSC and SORBS3. Increased expression of such genes can be used as a treatment for HCC or breast cancer.

In some embodiments of the methods, the isolated nucleic acid molecule includes a vector, such as an expression vector. Vectors can be of non-viral (for example, plasmids) or viral (for example, adenovirus, adeno-associated virus, retrovirus, herpes virus, vaccinia virus) origin. Suitable vectors, such as gene therapy vectors, are well known in the art.

Suitable viral vectors include, but are not limited to, adenovirus vectors, adeno-associated virus vectors, retroviral vectors, lentiviral vectors, herpesviral vectors, and the like. For example, adenovirus vectors can be first, second, third and/or fourth generation adenoviral vectors or gutless adenoviral vectors. Adenovirus vectors can be generated to very high titers of infectious particles; infect a great variety of cells; efficiently transfer genes to cells that are not dividing; and are seldom integrated in the host genome, which avoids the risk of cellular transformation by insertional mutagenesis (Douglas and Curiel, *Science and Medicine*, March/April 1997, pages 44-53; Zern and Kresinam, *Hepatology* 25(2), 484-491, 1997). Representative adenoviral vectors which can be used for the methods provided herein are described by Stratford-Perricaudet et al. (*J. Clin. Invest.* 90: 626-630, 1992); Graham and Prevec (In Methods in Molecular Biology: Gene Transfer and Expression Protocols 7: 109-128, 1991); and Barr et al. (*Gene Therapy*, 2:151-155, 1995), which are herein incorporated by reference.

Adeno-associated virus (AAV) vectors also are suitable for administration of HCC-associated genes. Methods of generating AAV vectors, administration of AAV vectors and their use are well known in the art (see, for example, U.S. Pat. No. 6,951,753; U.S. Pre-Grant Publication Nos. 2007-036757, 2006-205079, 2005-163756, 2005-002908; and PCT Publication Nos. WO 2005/116224 and WO 2006/119458, each of which is herein incorporated by reference).

Retrovirus, including lentivirus, vectors can also be used with the methods described herein. Lentiviruses include, but are not limited to, human immunodeficiency virus (such as HIV-1 and HIV-2), feline immunodeficiency virus, equine infectious anemia virus and simian immunodeficiency virus. Other retroviruses include, but are not limited to, human T-lymphotropic virus, simian T-lymphotropic virus, murine leukemia virus, bovine leukemia virus and feline leukemia virus. Methods of generating retrovirus and lentivirus vectors and their uses have been well described in the art (see, for example, U.S. Pat. Nos. 7,211,247; 6,979,568; 7,198,784; 6,783,977; and 4,980,289, each of which is herein incorporated by reference).

Suitable herpesvirus vectors can be derived from any one of a number of different types of herpesviruses, including, but not limited to, herpes simplex virus-1 (HSV-1), HSV-2 and herpesvirus saimiri. Recombinant herpesvirus vectors, their construction and uses are well described in the art (see, for example, U.S. Pat. Nos. 6,951,753; 6,379,6741 6,613,892; 6,692,955; 6,344,445; 6,319,703; and 6,261,552; and U.S. Pre-Grant Publication No. 2003-0083289, each of which is herein incorporated by reference).

B. Therapeutic Agents

Further provided is a method of identifying an agent for use in treating HCC, breast cancer of other solid tumor. As described herein, the method includes contacting a HCC cell or breast cancer cell with one or more candidate agents under conditions sufficient for the one or more candidate agents to alter expression or activity of at least one tumor-associated molecule (or HCC-associated molecule), detecting expression or activity of the at least one tumor-associated molecule in the presence of the one or more candidate agents, and comparing expression or activity of the at least one tumor-associated molecule in the presence of the one or more candidate agents to a control. An increase in expression or activity of one or more of SH2D4A, CCDC25, ELP3, DLC1, PROSC and SORBS3, or a decrease in expression or activity of one or more of HNRPD, PAQR3, PHF17 and DCK, relative to the control indicates that the one or more candidate agents is of use to treat HCC and/or breast cancer. In some examples, the control is a cell that is not contacted with the candidate agent or agents (also referred to as an untreated cell).

Therapeutic agents are agents that when administered in therapeutically effective amounts induce the desired response (e.g., treatment of a HCC tumor). In one example, therapeutic agents are specific binding agents that bind with higher affinity to a molecule of interest, than to other molecules. For example, a specific binding agent can be one that binds with high affinity to one or more tumor-associated genes, or a downstream factor that is regulated by one or more of the disclosed tumor-associated genes, but does not substantially bind to another gene or gene product. For example, the agent can interfere with gene expression (transcription, processing, translation, post-translational modification), such as, by interfering with the gene's mRNA and blocking translation of the gene product or by post-translational modification of a gene product, or by causing changes in intracellular localization. In another example, a specific binding agent binds to a protein encoded by one or more tumor-associated genes, or a downstream target of a HCC-associated gene, with a binding affinity in the range of 0.1 to 20 nM and reduces or inhibits the activity of such protein.

Contemplated herein is the use of specific binding agents to decrease expression or activity one or more tumor-associated genes whose down-regulation is correlated with a good prognosis (i.e., HNRPD, PAQR3, PHF17 and DCK). Specific binding agents can also be used to decrease expression or activity of a downstream target that is negatively regulated by one or more tumor-associated genes whose down-regulation is correlated with a poor prognosis (i.e., SH2D4A, CCDC25, ELP3, DLC1, PROSC and SORBS3).

Examples of specific binding agents include antisense compounds (such as antisense oligonucleotides, siRNAs, miRNAs, shRNAs and ribozymes), antibodies, ligands, recombinant proteins, peptide mimetics, and soluble receptor fragments. Methods of making specific binding agents that can be used clinically are known in the art.

Specific binding agents can be therapeutic, for example by reducing or inhibiting the biological activity of a tumor-associated nucleic acid or protein, or a nucleic acid or protein that is negatively regulated by a tumor-associated gene. For example, a specific binding agent that binds with high affinity to a tumor-associate gene, or a downstream target of a tumor-associated gene, may substantially reduce the biological function of the gene or gene product. In other examples, a specific binding agent that binds with high affinity to one of the proteins encoded by a tumor-associated gene, or a downstream target of a tumor-associated gene, may substantially reduce the biological function of the protein. Such agents can be administered in therapeutically effective amounts to subjects in need thereof, such as a subject having HCC.

C. Administration of Therapeutic Agents

Therapeutic agents can be administered to a subject in need of treatment using any suitable means known in the art. Methods of administration include, but are not limited to, intradermal, intramuscular, intraperitoneal, parenteral, intravenous, subcutaneous, vaginal, rectal, intranasal, inhalation, oral or by gene gun. Intranasal administration refers to delivery of the compositions into the nose and nasal passages through one or both of the nares and can comprise delivery by a spraying mechanism or droplet mechanism, or through aerosolization of the nucleic acid or virus. Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Therapeutic agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight and general condition of the subject, the particular therapeutic agent being used and its mode of administration. An appropriate dose can be determined by one of ordinary skill in the art using only routine experimentation.

VII. Methods of Identifying Therapeutic Agents

This disclosure concerns the identification of a ten gene driver signature that can be used to predict the prognosis of a subject with a solid tumor, such as HCC or breast cancer. A decrease in DNA copy number or mRNA expression of SH2D4A, CCDC25, ELP3, DLC1, PROSC or SORBS3 in a HCC or breast cancer tumor sample indicates a poor prognosis for the patient, while a decrease in DNA copy number or mRNA expression of HNRPD, PAQR3, PHF17 or DCK, indicates a good prognosis for the patient. Thus, it would be desirable to identify prospective agents that can increase the expression or activity of SH2D4A, CCDC25, ELP3, DLC1, PROSC or SORBS3, or decrease the expression or activity of HNRPD, PAQR3, PHF17 or DCK. In some examples, the therapeutic agent increases the expression or activity of SH2D4A, CCDC25, ELP3, DLC1, PROSC or SORBS3. In other examples, the therapeutic agent inhibits the expression or activity of a molecule that is negatively regulated by SH2D4A, CCDC25, ELP3, DLC1, PROSC or SORBS3. In other examples, the therapeutic agent decreases the expression or activity of HNRPD, PAQR3, PHF17 or DCK.

A. Representative Target Molecules

Therapeutic agents include agents that target a tumor-associated gene nucleic acid molecule or a polypeptide encoded thereby. Also contemplated are therapeutic agents that target a downstream factor regulated by a tumor-associated molecule. As described herein, tumor-associated molecules include SH2D4A, CCDC25, ELP3, DLC1, PROSC, SORBS3, HNRPD, PAQR3, PHF17 and DCK nucleic acid or protein sequences.

Polypeptides useful in the disclosed method are any known tumor-associated polypeptides or homologs, functional fragments, or functional variants thereof. A tumor-associated polypeptide homolog, functional fragment, or functional variant retains at least one biological function of the particular tumor-associated polypeptide (e.g., the biological function of SH2D4A, CCDC25, ELP3, DLC1, PROSC, SORBS3, HNRPD, PAQR3, PHF17 or DCK).

The amino acid sequences of SH2D4A, CCDC25, ELP3, DLC1, PROSC, SORBS3, HNRPD, PAQR3, PHF17 and DCK polypeptides and the nucleic acid sequences encoding the same are well known. GenBank Accession numbers of exemplary human SH2D4A, CCDC25, ELP3, DLC1, PROSC, SORBS3, HNRPD, PAQR3, PHF17 and DCK sequences are provided herein. Additional tumor-associated nucleic acid and protein sequences, including human sequences and sequences from other species, are publically available. Routine comparison (e.g., using BLASTP software, for amino acid sequence, or BLASTN software, for nucleic acid sequences) of these (or other) HCC-associated sequences against publicly available databases (such as GenBank non-redundant and/or patent databases) will reveal other tumor-associated molecule homologs. Any of these exemplary polypeptides are contemplated for use in the disclosed methods.

Exemplary SH2D4A, CCDC25, ELP3, DLC1, PROSC, SORBS3, HNRPD, PAQR3, PHF17 and DCK homologs or functional variants include polypeptides that share a particular degree of sequence identity with the human SH2D4A, CCDC25, ELP3, DLC1, PROSC, SORBS3, HNRPD, PAQR3, PHF17 and DCK polypeptide, or that involve the substitution, insertion or deletion of one or several amino acids in the human SH2D4A, CCDC25, ELP3, DLC1, PROSC, SORBS3, HNRPD, PAQR3, PHF17 or DCK polypeptide (including, e.g., splice variants).

In some method embodiments, a SH2D4A, CCDC25, ELP3, DLC1, PROSC, SORBS3, HNRPD, PAQR3, PHF17 or DCK polypeptide is a SH2D4A, CCDC25, ELP3, DLC1, PROSC, SORBS3, HNRPD, PAQR3, PHF17 or DCK homolog or functional variant having at least 60% amino acid sequence identity with the human SH2D4A, CCDC25, ELP3, DLC1, PROSC, SORBS3, HNRPD, PAQR3, PHF17 or DCK polypeptide; for example, some SH2D4A, CCDC25, ELP3, DLC1, PROSC, SORBS3, HNRPD, PAQR3, PHF17 or DCK variants will share at least 75%, at least 80%, at least 85%, at least 90%, at least 95%, or at least 98% amino acid sequence identity with the human SH2D4A, CCDC25, ELP3, DLC1, PROSC, SORBS3, HNRPD, PAQR3, PHF17 or DCK sequence.

In other method embodiments, a tumor-associated polypeptide is a tumor-associated functional variant having one or more conservative amino acid substitutions. Conservative substitutions are likely to have minimal impact on the activity of the resultant protein. Further information about conservative substitutions can be found, for instance, in Ben Bassat et al. (*J. Bacteriol.*, 169:751-757, 1987), O'Regan et al. (*Gene*, 77:237-251, 1989), Sahin-Toth et al. (*Protein Sci.*, 3:240-247, 1994), Hochuli et al. (*Bio/Technology*, 6:1321-1325, 1988) and in widely used textbooks of genetics and molecular biology. In some examples, a HCC-associated homolog or functional variants can have no more than 3, 5, 10, 15, 20, 25, 30, 40, or 50 conservative amino acid changes compared to the wild-type human sequences. The following table shows exemplary conservative amino acid substitutions:

| Original Residue | Conservative Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

With known tumor-associated molecule amino acid sequences and corresponding nucleic acid sequences, tumor-associated molecule homologs and variants are easily obtained by conventional molecular methods. For example, tumor-associated polypeptide homologs are naturally occurring and can be isolated by any of a myriad of protein purification techniques known in the art (for example, Scopes, *Protein Purification: Principles and Practice*, 3rd Edition, New York:Springer-Verlag, 1994; *Protein Purification Techniques*, 2nd Edition, ed. by Simon Roe, New York:Oxford University Press, 2001; *Membrane Protein Purification and Crystallization*, 2nd Edition, ed. by Hunte et al., San Diego: Academic Press, 2003). In other examples, a tumor-associated variant can be produced by manipulation of a known tumor-associated polypeptide-encoding nucleotide sequence using standard procedures, including without limitation the commonly known techniques of site-directed mutagenesis or PCR.

Some methods involve an endogenous tumor-associated polypeptide while others involve exogenous tumor-associated polypeptides. An endogenous tumor-associated polypeptide is naturally expressed in a cell, tissue, or subject. An exogenous tumor-associated polypeptide is not naturally expressed in a cell, tissue, or subject. An exogenous tumor-associated polypeptide may be expressed in a cell, tissue or subject by any known method; for example, an expression vector including a tumor-associated polypeptide-encoding nucleic acid sequence may be transfected (either stably or transiently) into a cell, tissue, or subject of interest.

Some method embodiments involve nucleic acid sequences encoding a tumor-associated polypeptide. It is common knowledge that a nucleic acid sequence can significantly differ from a prototype nucleic acid sequence and still encode the same, substantially the same, or a functionally equivalent polypeptide as the prototype sequence. Accordingly, other exemplary tumor-associated polypeptide-encoding nucleic acid sequences for use in a disclosed method have at least about 60%, at least about 70%, at least about 80%, at least about 90%, at least about 95%, or at least about 98% sequence identity with human tumor-associated gene sequence.

Another conventional way to describe related nucleic acid sequences is by their tendency to specifically hybridize to each other under particular hybridization stringency conditions. Thus, other exemplary tumor-associated polypeptide-encoding nucleic acid sequences for use in a disclosed method will hybridize to all or part of the human tumor-associated gene nucleic acid sequence under moderate stringency, medium stringency, high stringency or very high stringency conditions. In some instances, a hybridization probe will be at least about 30 contiguous nucleotides of a tumor-associated gene nucleic acid sequence (such as at least about 50, at least about 100, at least about 200, at least about 300, at least about 500 or at least about 600 contiguous nucleotides).

B. Exemplary Candidate Agents

An "agent" is any substance or any combination of substances that is useful for achieving an end or result; for example, a substance or combination of substances useful for modulating gene expression or protein activity. Any agent that has potential (whether or not ultimately realized) to modulate a tumor-associated molecule or a downstream factor regulated by a tumor-associated molecule is contemplated for use in the methods of this disclosure. For example, contemplated are agents that have potential to increase SH2D4A, CCDC25, ELP3, DLC1, PROSC or SORBS3 mRNA or protein expression, or enhance an activity of SH2D4A, CCDC25, ELP3, DLC1, PROSC or SORBS3. Also contemplated are agents that have potential to decrease HNRPD, PAQR3, PHF17 or DCK mRNA or protein expression, or inhibit an activity of HNRPD, PAQR3, PHF17 or DCK.

Exemplary candidate agents include, but are not limited to, peptides such as, for example, soluble peptides, including but not limited to members of random peptide libraries (see, e.g., Lam et al., *Nature*, 354:82-84, 1991; Houghten et al., *Nature*, 354:84-86, 1991), and combinatorial chemistry-derived molecular library made of D- and/or L-configuration amino acids, phosphopeptides (including, but not limited to, members of random or partially degenerate, directed phosphopeptide libraries; see, e.g., Songyang et al., *Cell*, 72:767-778, 1993), antibodies (including, but not limited to, polyclonal, monoclonal, humanized, anti-idiotypic, chimeric or single chain antibodies, and Fab, F(ab')$_2$ and Fab expression library fragments, and epitope-binding fragments thereof), small organic or inorganic molecules (such as, so-called natural products or members of chemical combinatorial libraries), molecular complexes (such as protein complexes), or nucleic acids.

Libraries (such as combinatorial chemical libraries) useful in the disclosed methods include, but are not limited to, peptide libraries (see, e.g., U.S. Pat. No. 5,010,175; Furka, *Int. J. Pept. Prot. Res.*, 37:487-493, 1991; Houghton et al., *Nature*, 354:84-88, 1991; PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Natl. Acad. Sci. USA*, 90:6909-6913, 1993), vinylogous polypeptides (Hagihara et al., *J. Am. Chem. Soc.*, 114:6568, 1992), nonpeptidal peptidomimetics with glucose scaffolding (Hirschmann et al., *J. Am. Chem. Soc.*, 114:9217-9218, 1992), analogous organic syntheses of small compound libraries (Chen et al., *J. Am. Chem. Soc.*, 116:2661, 1994), oligocarbamates (Cho et al., *Science*, 261: 1303, 1003), and/or peptidyl phosphonates (Campbell et al., *J. Org. Chem.*, 59:658, 1994), nucleic acid libraries (see Sambrook et al. *Molecular Cloning, A Laboratory Manual*, Cold Springs Harbor Press, N.Y., 1989; Ausubel et al., *Current Protocols in Molecular Biology*, Green Publishing Associates and Wiley Interscience, N.Y., 1989), peptide nucleic acid libraries (see, e.g., U.S. Pat. No. 5,539,083), antibody libraries (see, e.g., Vaughn et al., *Nat. Biotechnol.*, 14:309-314, 1996; PCT App. No. PCT/US96/10287), carbohydrate libraries (see, e.g., Liang et al., *Science*, 274:1520-1522, 1996; U.S. Pat. No. 5,593,853), small organic molecule libraries (see, e.g., benzodiazepines, Baum, C&EN, January 18, page 33, 1993; isoprenoids, U.S. Pat. No. 5,569,588; thiazolidinones and methathiazones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514) and the like.

Libraries useful for the disclosed screening methods can be produce in a variety of manners including, but not limited to, spatially arrayed multipin peptide synthesis (Geysen, et al., *Proc. Natl. Acad. Sci.*, 81(13):3998-4002, 1984), "tea bag" peptide synthesis (Houghten, *Proc. Natl. Acad. Sci.*, 82(15): 5131-5135, 1985), phage display (Scott and Smith, *Science*, 249:386-390, 1990), spot or disc synthesis (Dittrich et al., *Bioorg. Med. Chem. Lett.*, 8(17):2351-2356, 1998), or split and mix solid phase synthesis on beads (Furka et al., *Int. J. Pept. Protein Res.*, 37(6):487-493, 1991; Lam et al., *Chem. Rev.*, 97(2):411-448, 1997). Libraries may include a varying number of compositions (members), such as up to about 100 members, such as up to about 1000 members, such as up to about 5000 members, such as up to about 10,000 members, such as up to about 100,000 members, such as up to about 500,000 members, or even more than 500,000 members.

In one convenient embodiment, high throughput screening methods involve providing a combinatorial chemical or peptide library containing a large number of potential therapeutic compounds. Such combinatorial libraries are then screened in one or more assays as described herein to identify those library members (particularly chemical species or subclasses) that display a desired characteristic activity (such as, modulating expression or activity of SH2D4A, CCDC25, ELP3, DLC1, PROSC, SORBS3, HNRPD, PAQR3, PHF17 or DCK). The compounds thus identified can serve as conventional "lead compounds" or can themselves be used as potential or actual therapeutics. In some instances, pools of candidate agents may be identify and further screened to determine which individual or subpools of agents in the collective have a desired activity.

C. Assays

Screening methods may include, but are not limited to, methods employing solid phase, liquid phase, cell-based or virtual (in silico) screening assays. In one exemplary assay, compounds that modulate expression or activity of a tumor-associated molecule are identified. For instance, certain assays may identify compounds that modulate (e.g., increase or decrease) the expression of a tumor-associated gene nucleic acid (e.g., DNA or mRNA) or tumor-associated polypeptide, or that affect tumor-associated gene regulatory sequences so as to modify (e.g., increase or decrease) tumor-associated gene (and/or mRNA) expression.

It is to be understood that the disclosed methods involving the detection (or determination) of a change, modification, alteration, etc. (e.g., increase or decrease) in a particular composition or process, typically, are intended to be relative to a known or determined standard and/or control state, for example, as existed in the same test system prior to the addition of a test agent, or as existed in a comparable test system in the absence of a test agent.

Candidate agents are screened in a test system for their effect on expression or activity of a tumor-associated molecule. Such effects can be detected, for example, by increased expression of a tumor-associated gene or protein (SH2D4A, CCDC25, ELP3, DLC1, PROSC or SORBS3), decreased expression of a tumor-associated gene or protein (HNRPD, PAQR3, PHF17 or DCK), increased activity of a tumor-associated polypeptide (SH2D4A, CCDC25, ELP3, DLC1, PROSC or SORBS3), or decreased activity of a tumor-associated polypeptide (SH2D4A, CCDC25, ELP3, DLC1, PROSC or SORBS3).

A change in the expression of a tumor-associated nucleic acid (such as, a tumor-associated gene or transcript) or polypeptide can be determined by any method known in the art. For example, the levels of a tumor-associated gene transcript or tumor-associated polypeptide can be measured by standard techniques, such as, for RNA, Northern blot, PCR (including RT-PCR or q-PCR), in situ hybridization, or nucleic acid microarray, or, for protein, Western blot, antibody array, or immunohistochemistry. In some methods, the expression of a tumor-associated gene mRNA can also be increased or decreased by increased or decreased stability of the mRNA. In particular methods, the expression of a tumor-associated nucleic acid (such as, a tumor-associated gene or transcript) or polypeptide is increased or decreased when its level or activity is at least 10%, at least 20%, at least 30%, at least 50%, at least 100% or at least 250% higher or lower, respectively, than control measurements of the same indicator (e.g., in the same test system prior to addition of a test agent, or in a comparable test system in the absence of a test agent).

Also disclosed herein are methods of identifying agents that modulate the expression of a tumor-associated nucleic acid or a reporter gene operably linked to a tumor-associated gene transcriptional regulatory sequence. Generally, such methods involve contacting (directly or indirectly) with a candidate agent an expression system comprising a nucleic acid sequence encoding a tumor-associated polypeptide, or a reporter gene operably linked to a tumor-associated gene transcription regulatory sequence, and detecting a change (e.g., an increase or decrease) in the expression of the tumor-associated gene or reporter gene.

Modulation of the expression of a tumor-associated gene or gene product (e.g., transcript or protein) can be determined using any expression system capable of expressing a tumor-associated polypeptide or transcript (such as, a cell, tissue, or organism, or in vitro transcription or translation systems). In some embodiments, cell-based assays are performed. Non-limiting exemplary cell-based assays may involve test cells such as, cells (including cell lines) that normally express a tumor-associated gene, its corresponding transcript(s) and/or tumor-associated protein(s), or cells (including cell lines) that have been transiently transfected or stably transformed with a reporter construct driven by a regulatory sequence of a tumor-associated gene.

As mentioned above, some disclosed methods involve cells (including cell lines) that have been transiently transfected or stably transformed with a reporter construct driven by a regulatory sequence of a tumor-associated gene. A "regulatory sequence" as used herein can include some or all of the regulatory elements that regulate the expression of a particular nucleic acid sequence (such as, a tumor-associated gene) under normal circumstances. In particular examples, a regulatory region includes the contiguous nucleotides located at least 100, at least 500, at least 1000, at least 2500, at least 5000, or at least 7500 nucleotides upstream of the transcriptional start site of the regulated nucleic acid sequence (such as, a tumor-associated gene).

In method embodiments involving a cell transiently or stably transfected with a reporter construct operably linked to a tumor-associated gene regulatory region, the level of the reporter gene product can be measured. Reporter genes are nucleic acid sequences that encode readily assayed proteins. Numerous reporter genes are commonly known and methods of their use are standard in the art. Non-limiting representative reporter genes are luciferase, β-galactosidase, chloramphenicol acetyl transferase, alkaline phosphatase, green fluorescent protein, and others. In the applicable methods, the reporter gene product is detected using standard techniques for that particular reporter gene product (see, for example, manufacturer's directions for human placental alkaline phosphatase (SEAP), luciferase, or enhance green fluorescent protein (EGPF) available from BDBiosciences (Clontech); or galactosidase/luciferase, luciferase, or galactosidase available from Applied Biosystems (Foster City, Calif., USA); or available from various other commercial manufacturers of reporter gene products). A difference in the level and/or activity of reporter gene measured in cells in the presence or absence of a test agent indicates that the test agent modulates the activity of the TRB3 regulatory region driving the reporter gene.

VIII. Tumor and Non-Tumor Tissue Samples

The methods provided herein include detecting expression of one or more tumor-associated genes in solid tumors (such as HCC tumor and breast cancer tumors) and non-tumor tissue samples. In some embodiments, the tissue samples are obtained from subjects diagnosed with HCC or breast cancer and, in some cases, from healthy subjects or cadaveric donors. A "sample" refers to part of a tissue that is either the entire tissue, or a diseased or healthy portion of the tissue. As described herein, tumor tissue samples are compared to a control. In some embodiments, the control is non-tumor tissue sample obtained from the same subject, such as non-cancerous liver tissue surrounding the tumor. In other embodiments, the control is a colon tissue sample obtained from a healthy patient or a non-cancerous tissue sample from a cadaver. In other embodiments, the control is a standard or reference value based on an average of historical values. In some examples, the reference value is an average expression value in HCC or breast tumors obtained from a group of HCC or breast cancer patients with a poor prognosis.

Tissue samples can be obtained from a subject using any method known in the art. For example, tissue samples can be obtained from HCC or breast cancer patients who have undergone tumor resection (or mastectomy) as a form of treatment. From these patients, both tumor tissue and surrounding non-cancerous colon tissue can be obtained. In some embodiments, the non-tumor tissue sample used as a control is obtained from a cadaver. In other embodiments, the non-cancerous tissue sample is obtained from a healthy liver donor (see Kim et al., Hepatology 39(2):518-527, 2004).

In some embodiments, tissue samples are obtained by biopsy. Biopsy samples can be fresh, frozen or fixed, such as formalin-fixed and paraffin embedded. Samples can be removed from a patient surgically, by extraction (for example by hypodermic or other types of needles), by microdissection, by laser capture, or by any other means known in the art.

The following examples are provided to illustrate certain particular features and/or embodiments. These examples should not be construed to limit the disclosure to the particular features or embodiments described.

EXAMPLES

Applying Comparative Genomic Hybridization (CGH), frequent DNA copy number gains at 1q, 8q and 20q, and frequent DNA copy number losses at 1p, 4q, 8p, 13q, 16q and 17p, have been identified in HCC specimens of different etiologies and cell lines (Farazi and DePinho, Nat. Rev. Cancer 6:674-687, 2006). Although the oncogenes MDM4 (1q32), MYC(8q24), Jab1(8q), cIAP1 and Yap(11q22) as well as the tumor suppressors DLC1(8p22), RB1(13q14) and TP53(17p13) have been identified and validated, the 'driver' genes in most genomic aberrations remain unknown (Schlaeger et al., Hepatology 47:511-520, 2008; Patil et al., Carcinogenesis 26:2050-2057, 2005; Zender et al., Cell 125:1253-1267, 2006; Xue et al., Genes Dev. 22:1439-1444, 2008; Bruix et al., Cancer Cell 5:215-219, 2004).

Described in the Examples below is an integrative approach of high-resolution array-based CGH (arrayCGH) to identify genomic aberrations in HCC clinical specimens. The genomic aberration pattern identified in HCC samples was consistent with previous studies (Farazi and DePinho, Nat. Rev. Cancer 6:674-687, 2006). In addition, statistical analysis revealed that genomic aberrations of HCC with good prognosis differs greatly from HCC with poor prognosis. Global correlation analysis of arrayCGH and gene expression data led to the identification of cancer driver genes which are specific to HCC with poor prognosis. This signature of cancer 'driver' genes was able to predict poor outcome in an independent validation set. Thus, this cancer 'driver' signature allows for the development of diagnostic and prognostic clinical tools as well as the discovery of genotype-specific therapies for patients with HCC. The driver gene signature described herein is also predictive of breast cancer patient prognosis. Furthermore, two new tumor suppressor genes (SH2D4A and SORBS3) were identified that can be used for genotype-specific treatment of solid tumors, such as HCC.

Example 1

Materials and Methods

This example describes the experimental procedures used for the studies described in Examples 2 and 3.
Liver Samples and Clinical Data Hepatic tissues were obtained with informed consent from 256 HCC patients who underwent radical resection. The sample enrollment criteria included those with a history of HBV infection or HBV-related liver cirrhosis, HCC diagnosed by two independent pathologists, and detailed information on clinical presentation and pathological characteristics (including intrahepatic recurrence, intrahepatic venous metastasis, lymph node involvement and extrahepatic metastases). For 251 patients, disease-free and overall survival as well as the cause of death was obtained. Patients were randomly assigned into two cohorts, 180 patients (70%) were assigned to the validation cohort (cohort 2) and 76 (30%) to the arrayCGH cohort (cohort 1). ArrayCGH was conducted on 76 primary HCC samples (cohort 1). Gene expression profiles were conducted in primary HCC and corresponding non-tumor hepatic fresh frozen tissues from cohort 2 and 64 clinical specimens of cohort 1. The normal liver pool consisted of total mRNA from seven disease free liver donors.
RNA Isolation and Gene Expression Microarrays Total RNA was extracted from frozen tissues using TRIzol™ (Invitrogen, Carlsbad, Calif.) according to the manufacturer's protocol. RNA integrity for each sample was confirmed with the Agilent 2100 Bioanalyzer (Agilent Technologies, Palo Alto, Calif.). For microarray profiling, tumors and paired non-tumor tissues were profiled separately using a single channel array platform. Gene expression profiling of tumor and paired non-tumor samples of 22 patients of cohort 1 and the normal liver pool were carried out on Affymetrix GeneChip™ HG-U133A 2.0 arrays (Affymetrix, Santa Clara, Calif.) according to the manufacturer's protocol. The fluorescent intensities were determined with an Affymetrix GeneChip™ Scanner 3000, controlled by GCOS Affymetrix software. All tumor and paired non-tumor samples of cohort 1 and cohort 2 were processed on the 96 HT HG-U133A 2.0 microarray platform. The fluorescent intensities were determined with an Affymetrix GeneChip™ HT Array Plate Scanner, controlled by GCOS Affymetrix software. Quality controls included image inspection as well as Relative Log Expression (RLE) and Normalized Unscaled Standard Error (NUSE) implemented in the affyPLM package available at the Bioconductor (www.bioconductor.org). By applying the quality standards, 13 arrays were excluded (4 non-tumor tissues of cohort 1 and 9 non-tumor tissues of cohort 2). In accordance with Minimum Information About a Microarray Experiment (MIAME) guidelines, the CEL files for the microarray data and additional patient information were deposited into the Gene Expression Omnibus (GEO) repository. The Affymetrix datasets of Karolinska (GSE1456), Uppsala (GSE3494, GSE4922), Rotterdam (GSE2034), TRANSBIG (GSE7390) and Mainz (GSE1121) studies were previously described (Pawitan et al., *Breast Cancer Res.* 7:R953-R964, 2005; Ivshina et al., *Cancer Res.* 66, 10292-10301, 2006; Miller et al., *Proc. Natl. Acad. Sci. U.S.A.* 102:13550-13555, 2005; Wang et al., *Lancet* 365:671-679, 2005; Desmedt et al., *Clin. Cancer Res.* 13:3207-3214, 2007; Schmidt et al., *Cancer Res.* 68:5405-5413, 2008).

DNA Isolation and ArrayCGH

Genomic DNA was isolated using proteinase K digestion (P2308, Sigma-Aldrich, St. Louis, Mo.) and subsequent phenol/chloroform extraction. Purified DNA was quantified by the fluorometric assay Quant-iT Pico Green dsDNA (Invitrogen, Carlsbad, Calif.). Fluorescence was measured with an excitation wavelength of 485 nm and an emission wavelength of 535 nm (Wallac Victor2, Perkin Elmer, Shelton, Conn.). DNA concentrations were calculated from a standard curve of double-stranded control DNA provided with the kit. Five micrograms of genomic DNA and reference DNA of the opposite gender (human genomic DNA, Promega, San Luis Obispo, Calif.) were digested with the restriction enzymes AluI and RsaI. Digested DNA was purified using QIAprep Spin Miniprep Kit (QIAGEN, Valencia, Calif.) and labeled using the BioPrime™ Array CGH Genomic Labeling kit (Invitrogen, Carlsbad, Calif.) according to the manufacturer's instructions in a volume of 50 µl with a modified dNTP mix containing 120 µM each of dATP, dGTP, and dCTP; 60 µM dTTP; and 60 µM Cy5-dUTP (GE Amersham, Piscataway, N.J.) or Cy3-dUTP (GE Amersham, Piscataway, N.J.). Tumor and reference DNA were pooled, purified and concentrated to 79 µl using Vivaspin 500 concentrator (VS0122, 30k MWCO, Vivascience, Littleton, Mass.). Twenty-five µg Cot-1 DNA (Invitrogen, Carlsbad, Calif.) were added and then mixed with 1/10 volume of 10× blocking agent (Agilent, Santa Clara, Calif.) and an equal amount of 2× hybridization buffer (Agilent, Santa Clara, Calif.), denatured at 95° C. for 5 minutes and pre-incubated at 37° C. for 30 minutes in a water bath. Hybridizations were carried out on Human Genome CGH 105A Oligo Microarray glass slides (G4412A, Agilent, Santa Clara, Calif.). DNA samples were hybridized onto the array for 36-40 hours at 65° C. utilizing the DNA Microarray Hybridization Chamber SureHyb™ and Hybridization Oven (Agilent, Santa Clara, Calif.). After hybridization arrays were disassembled at room temperature, they were subsequently washed in wash solution 1 (0.5×SSPE and 0.005% N-Lauroylsarcosine) at room temperature for 5 minutes and wash solution 2 (0.1×SSPE and 0.005% N-Lauroylsarcosine) at 37° C. for 1 minute. Dried array slides were scanned using the DNA Microarray Scanner (Agilent, Santa Clara, Calif.). Raw image files of the arrays were processed using Feature Extraction software 8.1 (Agilent, Santa Clara, Calif.). Arrays with derivative log ratio spread (DLRS) higher than 0.2 log units were repeated and according to MIAME guidelines, raw data Feature Extraction files were deposited into the GEO repository.

Analyses and Statistics

The sex chromosomes were excluded from the analysis because the opposite gender was used as a reference. To identify chromosomal regions with altered copy numbers in single arrays, median normalization was applied using the R package snapCGH followed by segmentation and centralization. For segmentation and centralization of arrayCGH data, the signal intensities of the tumor and reference samples were preprocessed and normalized by the Agilent feature extraction software followed by segmentation analysis using the snapCGH R package available at the Bioconductor (www.bioconductor.org). The algorithms were implemented in the R programming language (www.r-project.org). The results were obtained using R version 2.6.2 and the DNAcopy library provided by the Bioconductor project (www.bioconductor.org), version 1.7. In brief, the intensity ratios of the tumor over reference samples were logarithm-2 (log 2) transformed and median-centered, and subjected to an improved circular binary segmentation (CBS) algorithm (Venkatraman and Olshen, *Bioinformatics* 23:657-663, 2007). Segments without significant statistical differences were then merged into the same states using the method provided by Willenbrock and Fridlyand (Willenbrock and Fridlyand, *Bioinformatics* 21: 4084-4091, 2005). Centers of the segmentation means for individual arrays were determined by setting the mode of density distribution as the baseline (log 2 ratio=0). The DNA copy number aberrations at particular genomic locations were determined by the corresponding segmentation means. Regions with segmented log 2 ratios greater than 0.5 and smaller than −0.5 were considered regions of gain and loss, respectively.

Affymetrix gene expression arrays obtained from different platforms were combined with the matchprobes package. Raw gene expression data were normalized using the Robust Multiarray Average (RMA) method and global median centering (Irizarry et al., *Biostatistics* 4:249-264, 2003). For genes with more than one probe set, the mean gene expression was calculated. To systematically identify genes whose expression was attributed by copy number alteration across the samples, the Pearson correlation coefficients (r) were calculated for each gene between the segmented log 2 ratios and the expression values. For each gene, data were randomly permuted 1000 times, and the empirical null distribution was obtained by the Pearson correlation coefficients calculated from all the random permutations. The distribution of r of all calculated genes in these experiments, along with the null distribution, was plotted. Genes with correlation coefficients greater than the one corresponding to the $99^{th}$ percentile of the empirical null distribution were considered positively correlated between DNA copy number alteration and expression.

For unsupervised hierarchical clustering of the arrayCGH data, segmented data was converted to 1, −1, 0 according to their respective status of gain, loss and no change, and then weighted by the squares of the frequencies of copy number gain or loss at a particular genomic location. Adjacent probes with identical DNA copy number profiles across all samples were combined to form unique segments. Average-linkage clustering was performed based on the Euclidean distance metric. Pearson correlation was used for Multidimensional Analysis (MDS). The significance of the difference in gain/loss status between HCC subgroups in unique segments was determined by the fisher's exact test and the p-values were adjusted using Benjamini-Hochberg correction. Adjacent significant regions with gaps less than 50 kb were combined and considered as one large region with differential genomic aberrations between subgroups.

Class prediction was performed in BRB-Array Tools. Six class prediction algorithms, i.e., Support Vector Machines (SVM), Compound Covariate Predictor (CCP), Diagonal Linear Discriminant (DLD), 1-Nearest Neighbor (1NN), 3-Nearest Neighbor (3NN) or Nearest Centroid (NC), were used to determine whether mRNA expression patterns could accurately discriminate good and poor survival HCC in an independent data set. In these analyses, arrayCGH cases for which gene expression data was available (N=64) were chosen to build a classifier which was then used to predict the cases of an independent cohort (N=180). The models incorporated genes that were differentially expressed among genes at the 0.001 significance level as assessed by the random variance t-test. In these analyses, 90% of the samples were randomly chosen to build a classifier which was then used to predict the remaining 10% cases of the training set. The accuracy of the prediction was calculated after 1000 repetitions of this random partitioning process for controlling number and proportion of false discoveries.

Analysis of gene expression from breast cancer datasets was performed by using BRB ArrayTools. The Affymetrix datasets Karolinska (GSE1456), Uppsala (GSE3494, GSE4922), Rotterdam (GSE2034), TRANSBIG (GSE7390) and Mainz (GSE1121) were downloaded from GEO. Data were filtered to exclude any probe set that was not a component of the 10-'driver' gene signature. Unsupervised clustering of each dataset was performed by using the samples only clustering option of BRB ArrayTools. Clustering was performed by using average linkage, the centered correlation metric and center the genes analytical option. Samples were assigned into two groups based on the first bifurcation of the cluster dendrogram.

The Kaplan-Meier survival analysis was performed to compare patient survival using GraphPad Prism™ software 5.0 (GraphPad Software, San Diego, Calif.) and the statistical p values were generated by the Cox-Mantel log-rank test. Cox proportional hazards regression was used to analyze the effect of clinical variables on patient survival using STATA 9.2 (College Station, Tex.). Clinical variables included age, sex, HBV active status, pre-resection alphafetoprotein (AFP), cirrhosis, alanine transferase (ALT), tumor size, nodular type and the HCC prognosis staging systems CLIP, BCLC and TNM classification (International Union Against Cancer, 2002). An AFP cutoff of 20 ng/mL, ALT of 50 U/L and tumor size of 5 cm were used in Cox regression analysis and are clinically relevant values used to distinguish patient survival. A univariate test was used to examine the influence of the 'driver' gene predictor or each clinical variable on patient survival. A multivariate analysis was performed to estimate the hazards ratio of the predictor while controlling for clinical variables that were significantly associated with survival in the univariate analysis. Since tumor size and nodular type were collinear with tumor staging, these variables were not included in the multivariate analysis. It was determined that the final model met the proportional hazards assumption. The statistical significance was defined as p<0.05.

Example 2

Identification of a Gene Signature for Predicting HCC and Breast Cancer Prognosis This example describes the identification of a 10-gene signature that can be used as an independent predictor of HCC and breast cancer patient survival.

Copy Number Aberrations and Gene Expression in HCC Exhibit High Correlation

A genome-wide search was applied for functional 'driver' genes whose disruption is linked to patient outcome among 256 HCC cases. These cases were randomly partitioned to a training/test set (cohort 1, N=76, 30%) and an independent validation set (cohort 2, N=180, 70%) whose clinical parameters did not differ (Table 1).

TABLE 1

Clinical Characteristics of the Subjects

| Clinical variable | Cohort 1 (N = 76) | Cohort 2 (N = 180) | P value |
|---|---|---|---|
| Gender | | | |
| Female | 8 | 26 | |
| Male | 68 | 154 | 0.546[a] |
| Age in years | | | |
| Median (range) | 50 (25-77) | 50 (21-74) | 0.338[b] |
| ALT | | | |
| Negative (≤50 U/L) | 42 | 110 | |
| Positive (>50 U/L) | 34 | 70 | 0.327[a] |
| HBV | | | |
| Negative | 0 | 6 | |
| Positive | 56 | 171 | 0.340[a] |
| No data | 20 | 3 | |
| Tumor size | | | |
| ≤5 cm | 40 | 117 | |
| >5 cm | 36 | 62 | 0.067[a] |
| No data | 0 | 1 | |
| Multi-nodular | | | |
| No | 55 | 146 | |
| Yes | 21 | 34 | 0.135[a] |
| Cirrhosis | | | |
| No | 4 | 18 | |
| Yes | 71 | 162 | 0.328[a] |
| No data | 1 | 0 | |
| TNM stage | | | |
| I | 20 | 79 | |
| II | 18 | 63 | |
| III-IV | 18 | 36 | 0.173[c] |
| No data | 20 | 2 | |
| AFP | | | |
| Negative (≤20 ng/mL) | 24 | 56 | |
| Positive (>20 ng/mL) | 51 | 121 | 1.000[a] |
| No data | 1 | 3 | |
| Adjuvant Therapy | | | |
| Yes | 11 | 30 | |
| No | 48 | 148 | 0.843[a] |
| No data | 17 | 2 | |
| Survival in months | | | |
| Median (range) | 62 (2-65) | >67 (2-67)[d] | 0.327[e] |

[a]Fisher's exact test;
[b]Un-paired t-test;
[c]Chi-square test;
[d]not estimateable;
[e]Log-rank test ArrayCGH was performed on cohort 1 using the high resolution Agilent 105A array platform (FIG. 1A). Consistent with previous publications (Schlaeger et al., *Hepatology* 47:511-520, 2008; Patil et al., *Carcinogenesis* 26:2050-2057, 2005), recurrent gains and losses on chromosomes 1q, 6p, 8q and 4q, 8p, 13q, 16, 17p, respectively, were identified (FIG. 1D). A total of 2666 genes (1130 gained; 1536 lost) were mapped to these regions and found in more than 20% of the clinical specimens assayed.

The gene list was next restricted to potential 'driver' genes using two criteria: (1) their expression in tumor, but not adjacent non-tumor specimens, should correlate with copy number changes (adjacent non-tumor tissues were included to account for a possible expression contribution by infiltrating non-cancerous cells); and (2) their expression should be associated with patient prognosis (overall or disease-free survival). The gene expression profiles of the tumor and non-tumor tissues were available for 64 samples in cohort 1. The density distribution of Pearson correlation coefficients was obtained and plotted for 10841 genes present on both the arrayCGH and mRNA microarrays (FIG. 1B). The mean of all Pearson's coefficients was 0.18 (95% confidence interval: 0.178 to 0.185). A correlation coefficient of 0.3, corresponding to the $99^{th}$ percentile of the 1000-fold random permutation, was used as the cutoff threshold for positive correlation. A total of 2959 genes (27.3% of all genes) met these criteria and were considered positively correlated. To ensure that the observed correlations were tumor-specific, Pearson correlation of the tumors' genomic aberration and the paired non-tumor tissue expression values were calculated. The distribution of the resulting Pearson coefficients from the non-tumor overlapped with the random distribution and only 95 genes (0.9% of all genes) had correlation coefficients exceeding 0.3, suggesting that the positive correlation was tumor-specific (FIG. 1C). Overall, among the 2959 correlating genes, 743 were up-regulated and 287 genes were down-regulated based on a 2-fold cutoff when compared to normal liver pools (FIG. 1D).

Figure 2C:
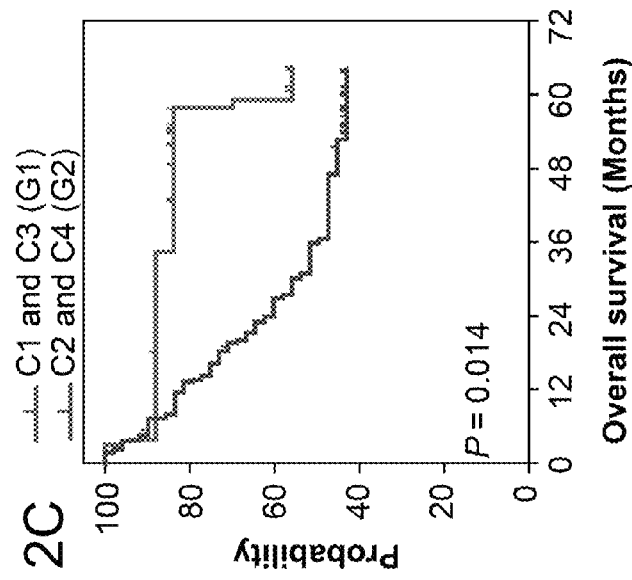
FIG. 2C is a graph showing Kaplan-Meier survival analysis of these four clusters, which reveals that clusters C1 and C3 have good prognosis, whereas, clusters C2 and C4 have poor prognosis. The statistical p-value was generated by the Cox-Mantel log-rank test.
Figure 2B:
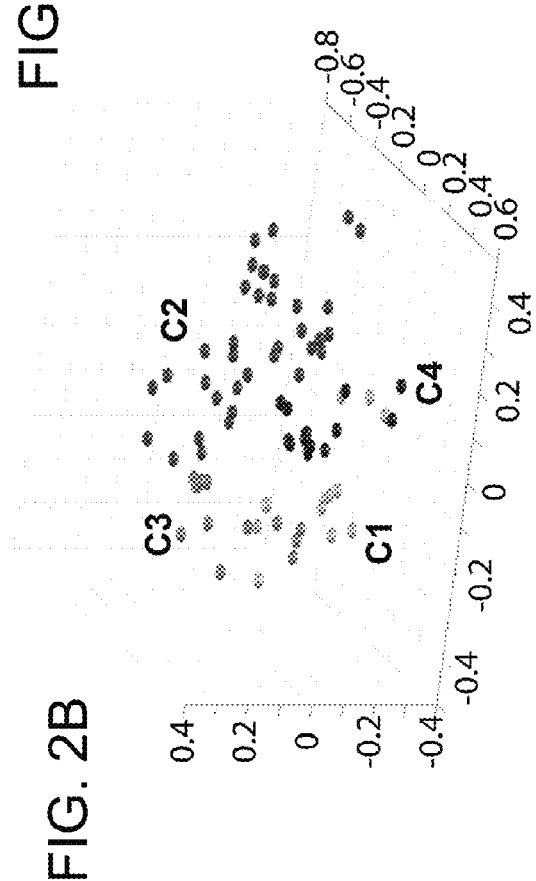
FIG. 2B is a graph of multidimensional scaling (MDS) showing close positioning of clusters C1 and C3 as well as of clusters C2 and C4.
Figure 7:
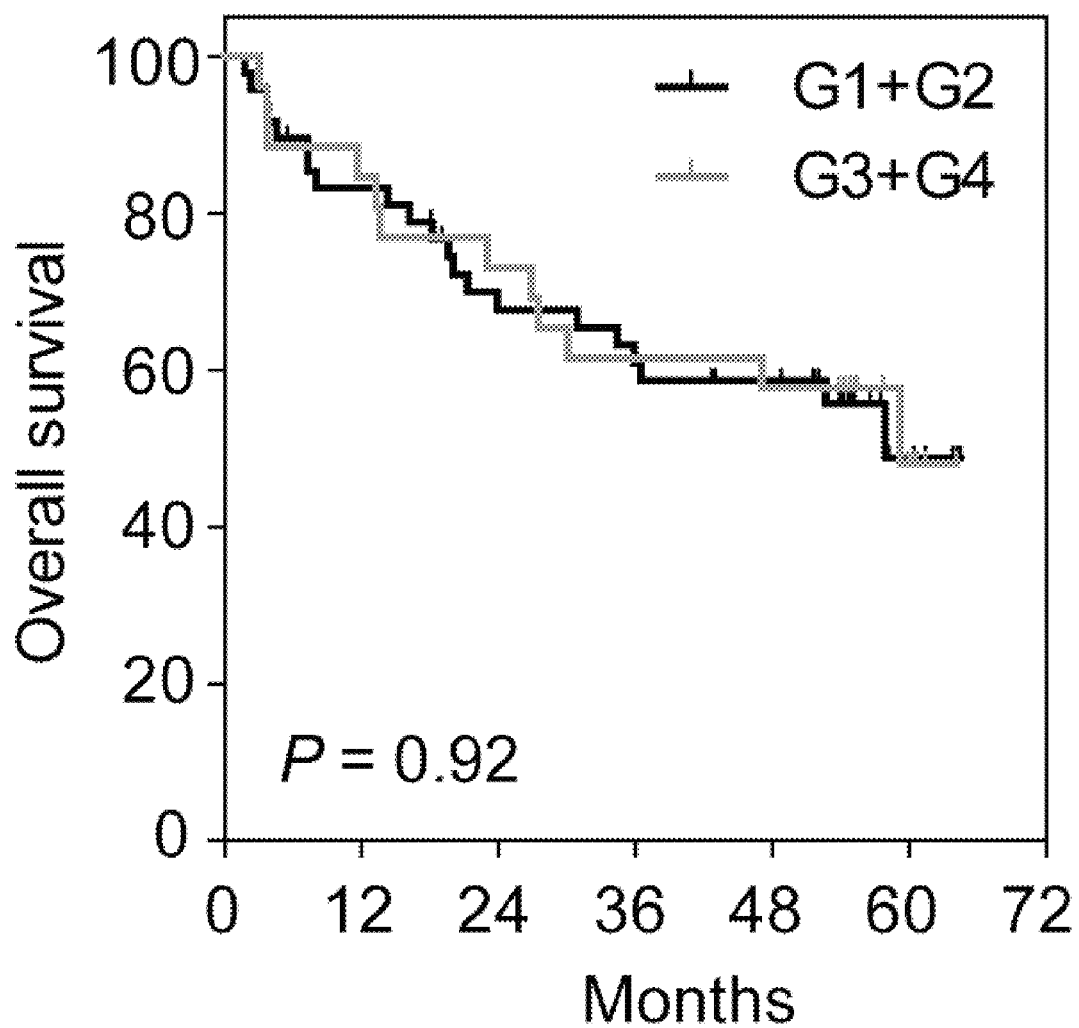
FIG. 7 is a graph showing analysis of overall survival of the first arrayCGH dendrogram branch, which exhibited no overall survival difference. Kaplan-Meier survival analysis reveals that overall survival prognosis of clusters C1 and C2 is similar to survival prognosis of clusters C3 and C4. The statistical p-value was generated by the Cox-Mantel log-rank test.
Figure 8A:
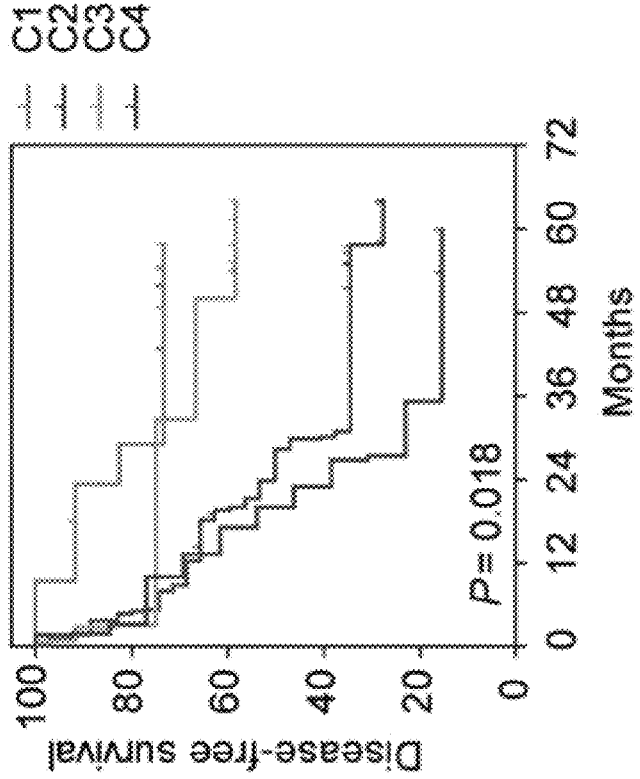
FIGS. 8A and 8B are graphs showing Kaplan-Meier survival analyses, which reveal that clusters C1 and C3 have good overall and disease-free survival prognosis, whereas, clusters C2 and C4 have poor prognosis. The statistical p-value was generated by the Cox-Mantel log-rank test.
Figure 8B:
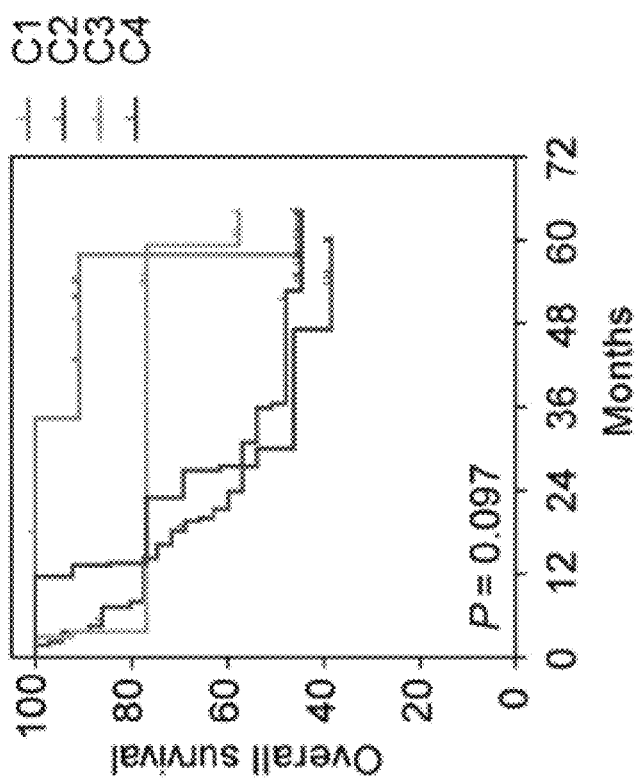
Figure 9A:
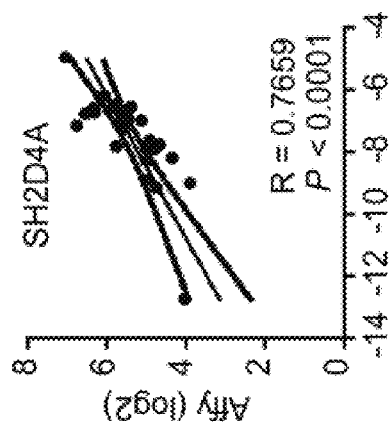
FIGS. 9A-9F are graphs showing the correlation of Affymetrix microarray data and qRT-PCR data of SH2D4A, CCDC25, ELP3, DLC1, PROSC and SORBS3, respectively. Pearson's correlation r-values and p-values are depicted.
Figure 9B:
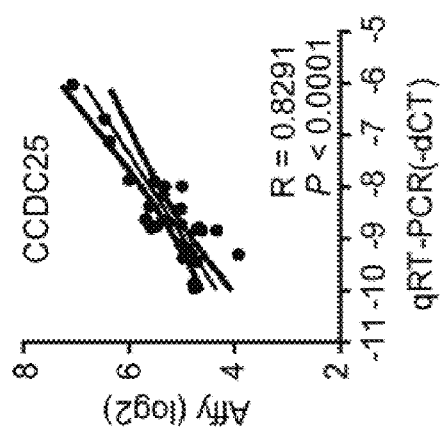
Figure 9C:
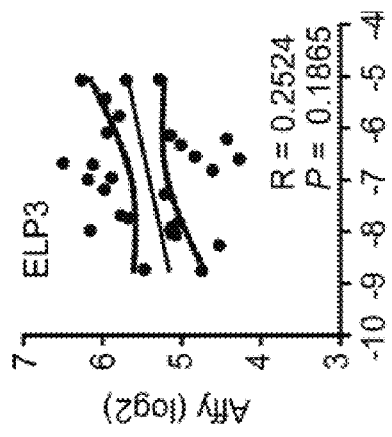
Figure 9D:
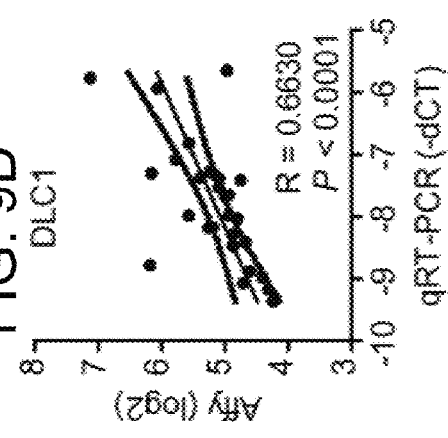
Figure 9E:
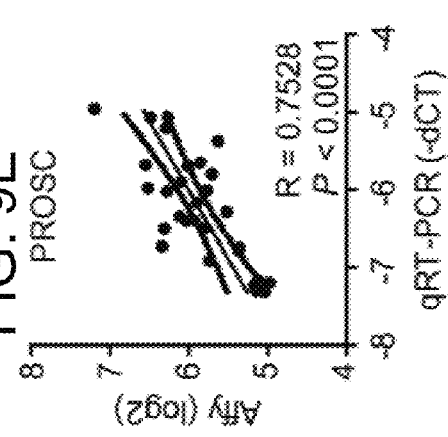
Figure 9F:
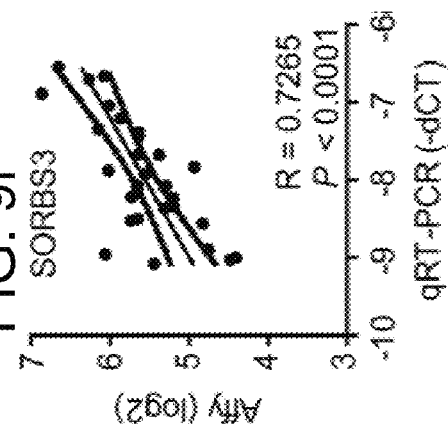
Figure 10A:
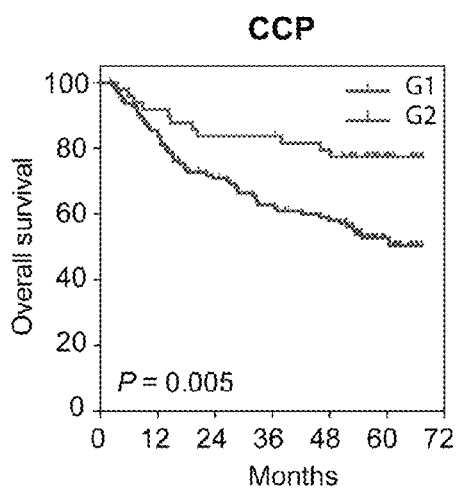
FIGS. 10A-10D are graphs showing performance of the survival gene signature excluding DLC1. Kaplan-Meier overall survival on the independent validation cohort 2 by predicted classification of G1 and G2 is shown. Prediction algorithms used were Compound Covariate Predictor (CCP), Linear Discriminant Analysis (LDA), Nearest Centroid (NC) and Support Vector Machines (SVM), respectively. The statistical p-value was generated by the Cox-Mantel log-rank test.
Figure 10B:
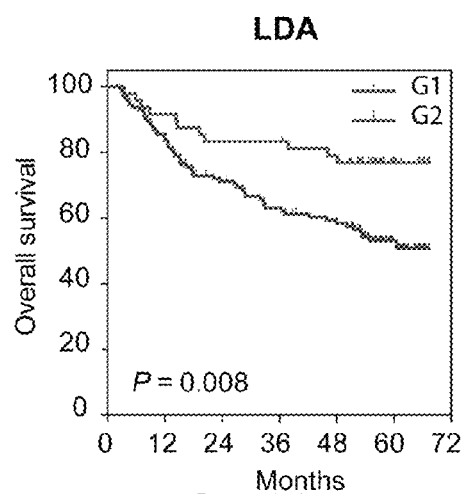
Figure 10C:
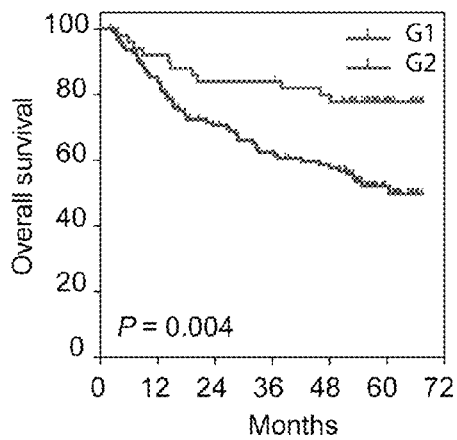
Figure 10D:
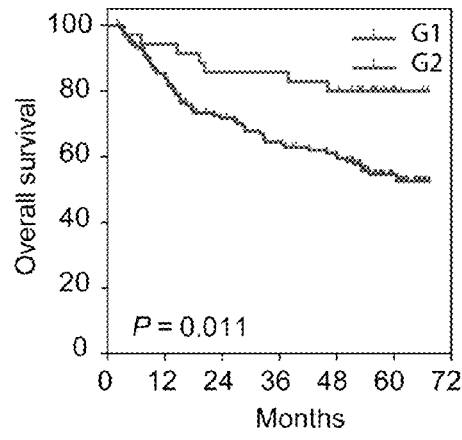

The Genomic Profiles of Good and Poor Outcome Subgroups Differ in Regions of Copy Number Loss It was postulated that 'driver' genes should be functionally selected and retained in tumors with an aggressive outcome. To test this hypothesis, unsupervised hierarchical clustering analysis was performed with arrayCGH data (FIG. 2A). It was found that cases separated by the first dendrogram branch differed mainly by gain of 1q (FIG. 2A). However, survival analysis of the first dendrogram branch (case separation into two major clusters) showed no overall survival difference (FIG. 7; p=0.92). Further subdivision yielded four subgroups, C1 to C4, which differed in their survival outcome. The estimated median survival and Kaplan-Meier analysis showed that overall and disease-free survival of clusters C1 and C3 was longer than that of C2 and C4 (FIG. 8 and Table 2). Moreover, multidimensional scaling analysis based on genomic profiles revealed a close proximity of clusters C1 and C3 as well as C2 and C4 (FIG. 2B). It therefore appeared that the samples could be divided into two major survival subtypes, i.e., G1 (good survival; C1 and C3) and G2 (poor survival; C2 and C4). Consistently, Kaplan-Meier survival analysis revealed that G2 had significantly worse survival than G1 (FIG. 2C).

TABLE 2

Clinical Characteristics of ArrayCGH Clusters C1 to C4[a]

| Clinical variable | C1 (N = 12) | C2 (N = 36) | C3 (N = 13) | C4 (N = 13) | P value |
|---|---|---|---|---|---|
| Survival | | | | | |
| Median [months] | 57.9 | 36.5 | >60[b] | 30.1 | 0.094[c] |
| Events (percent) | 2 (16.7%) | 19 (52.8%) | 4 (30.8%) | 8 (61.5%) | |
| Recurrence | | | | | |
| Median [months] | >60[b] | 28.4 | >60[b] | 20 | 0.018[c] |
| Events (percent) | 3 (25%) | 23 (63.9%) | 5 (38.5%) | 11 (84.6%) | |

Figure 3A:
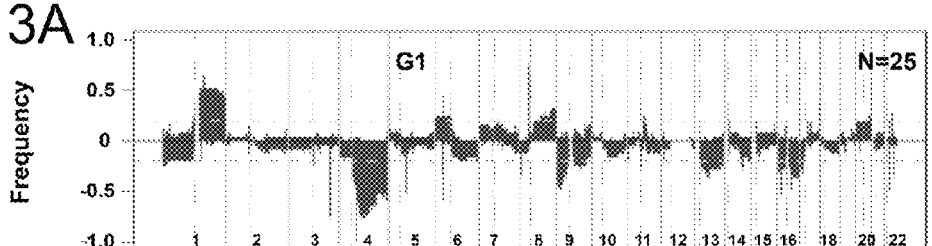
FIGS. 3A and 3B are graphs showing the frequency of significant increases in genome copy number plotted as a function of genome location for G1 (good survival) and G2 (poor survival) HCC subgroups, respectively. Positive values indicate frequencies of samples showing copy number increases [log 2(copy number)>0.5] and negative values indicate frequencies of samples showing copy number decreases [log 2(copy number)<−0.5].
Figure 3B:
Figure 3C:
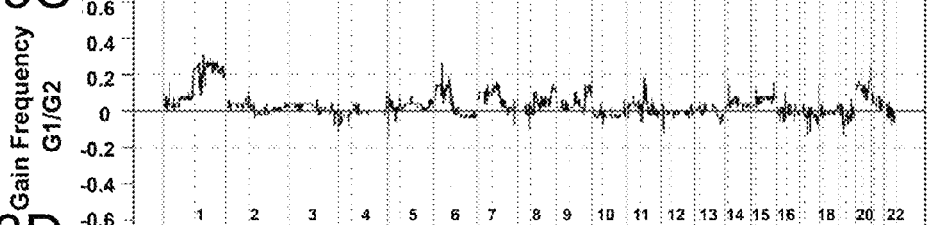
FIGS. 3C and 3D are graphs showing the differences (y axis) between frequencies of gain and loss across the genome for G1 versus G2 subtypes. Genome copy number aberration frequencies are plotted as a function of location position in the genome with positive values indicating higher frequencies in G1 over G2.
Figure 3D:
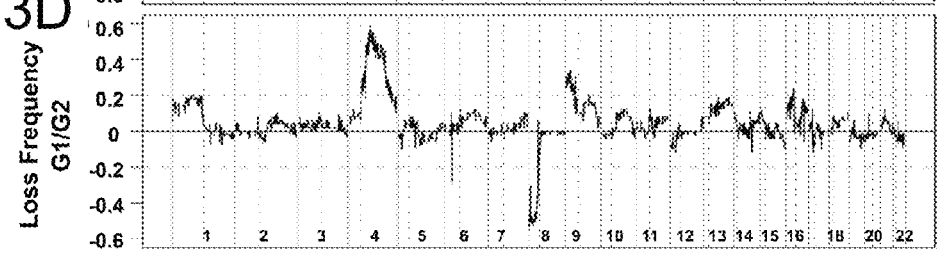

[a]There was no survival data available for two patients
[b]not estimable
[c]Log-rank test Next, the genomic aberration frequency was compared in the two subtypes (FIGS. 3A and 3B). While the gained regions appeared to be similar in G1 and G2, the lost regions showed up to a 60% difference (FIGS. 3C and D). It appeared that 4q loss was mainly associated with G1 while 8p loss was mainly associated with G2. Regions with significant difference between G1 and G2 were searched by applying two criteria: (1) The frequency of genomic aberrations had to differ by at least 20% between G1 and G2 and (2) the adjusted p-value had to be less than 0.05 (Benjamini-Hochberg correction). The regions identified were located on 1p, 4q, 8p and 9p (Table 3). Interestingly, all of the regions that were significantly different between G1 and G2 were lost. This suggested that survival related regions were associated with genomic loss and therefore, perhaps locations which are containing TSGs. Among 578 genes that mapped to these loss regions, 419 had expression data and among these, 134 (31.98%) showed significant correlation with genomic changes.

TABLE 3

Minimal aberrant regions significantly different between G1 and G2

| Cytoband | Size [Mb] | G1 [%] | G2 [%] | Difference [%] | P value[a] | Number of Genes | Correlating Genes |
|---|---|---|---|---|---|---|---|
| 1p31.1-p22.3 | 8.07 | 20 | 0 | −20 | 0.048 | 25 | 8 |
| 1p13.3 | 0.87 | 20 | 0 | −20 | 0.048 | 14 | 3 |
| 1p13.1 | 0.01 | 20 | 0 | −20 | 0.048 | 2 | 0 |
| 4q11-q12 | 0.68 | 32 | 4 | −28 | 0.031 | 4 | 1 |
| 4q12 | 3.22 | 32-36 | 4-6 | −(32-28) | 0.013-0.031 | 16 | 2 |

TABLE 3-continued

Minimal aberrant regions significantly different between G1 and G2

| Cytoband | Size [Mb] | G1 [%] | G2 [%] | Difference [%] | P value[a] | Number of Genes | Correlating Genes |
|---|---|---|---|---|---|---|---|
| 4q13.1 | 1.47 | 44 | 10 | −34 | 0.031 | 1 | 0 |
| 4q13.1-q13.2 | 4.43 | 44-60 | 10-12 | −(50-34) | 0.001-0.031 | 12 | 2 |
| 4q13.2-q31.21 | 72.28 | 56-76 | 10-22 | −(60-38) | 0.001-0.026 | 292 | 57 |
| 8p23.3-p23.1 | 6.98 | 4-12 | 45-63 | 41-55 | 0.001-0.005 | 22 | 1 |
| 8p23.1-p12 | 27.46 | 12 | 49-65 | 37-53 | 0.001-0.031 | 147 | 40 |
| 8p12 | 0.11 | 8 | 47 | 39 | 0.014 | 1 | 0 |
| 8p12-p11.23 | 3.38 | 4-8 | 39-49 | 35-41 | 0.005-0.045 | 27 | 9 |
| 8p11.22 | 0.11 | 4 | 35-37 | 31-33 | 0.031-0.05 | 1 | 0 |
| 9p24.2-p24.1 | 1.33 | 40 | 8 | −32 | 0.048 | 9 | 2 |
| 9p24.1-p23 | 5.04 | 44 | 10-12 | −(34-32) | 0.031-0.049 | 15 | 4 |
| 9p23 | 0.63 | 44 | 10-12 | −(34-32) | 0.031-0.049 | 0 | 0 |
| 9p23 | 1.40 | 48 | 12 | −36 | 0.024 | 3 | 1 |
| 9p23-p21.3 | 8.64 | 44-48 | 6-12 | −(38-32) | 0.005-0.049 | 41 | 10 |
| 9p21.3 | 0.46 | 44 | 12 | −32 | 0.049 | 2 | 0 |
| 9p21.1 | 0.46 | 36 | 6 | −30 | 0.031 | 1 | 0 |
| 9p21.1-p13.3 | 1.03 | 32 | 4 | −28 | 0.031 | 16 | 8 |
| 9p13.2-p13.1 | 1.53 | 32-36 | 4 | −(32-28) | 0.013-0.031 | 9 | 1 |

Three segments which did not contain any known genes were not included in this table
[a]Fisher's exact test.

Figure 3E:
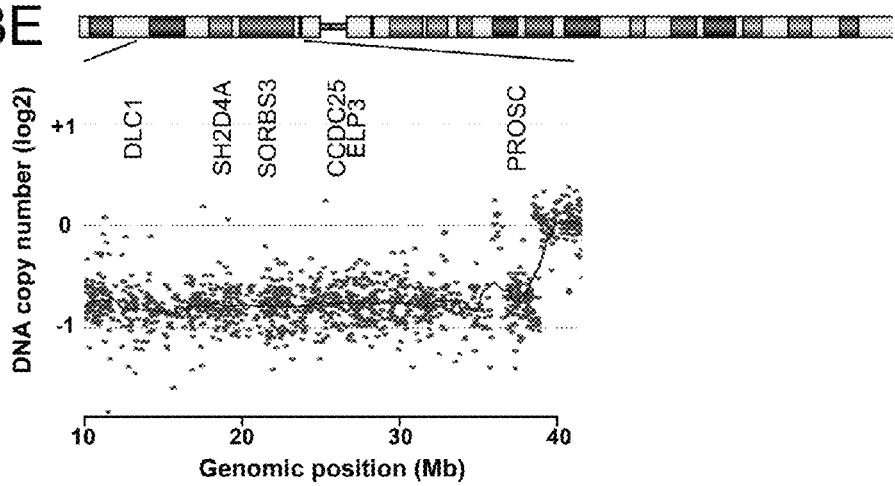
FIG. 3E illustrates a representative case with chromosome 8p deletion containing DLC1, SH2D4A, SORBS3, CCDC24, ELP3 and PROSC. Dots represent single probes, dots above the dashed line represent amplified and dots below the dashed line represent lost genomic regions.
Figure 5A:
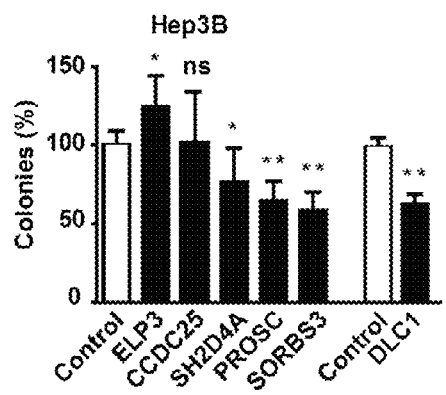
FIGS. 5A and 5B are graphs showing colony formation assay results from Hep3B and HuH1 cells transfected with vector control, ELP3, CCDC25, SH2D4A, PROSC, SORBS3 or DLC1.
Figure 5B:
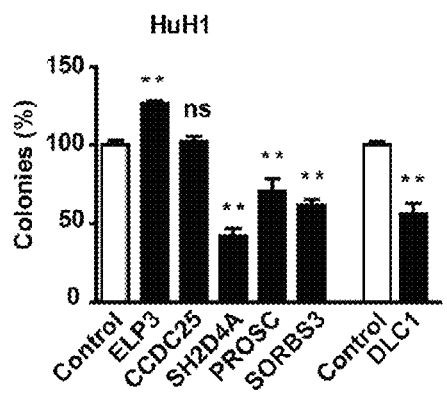
Figure 5C:
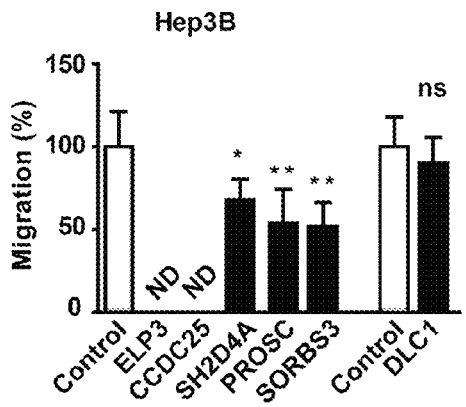
FIGS. 5C and 5D are graphs showing cell migration assay results from Hep3B and HuH1 cells transfected with vector control, ELP3, CCDC25, SH2D4A, PROSC, SORBS3 or DLC1. Data represent averages±SD. Colony formation and migration assays were performed in quintuplets for Hep3B and in triplicates for HuH1.
Figure 5D:
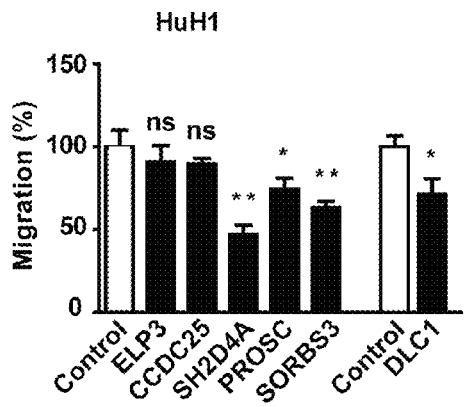

The Survival Gene Signature Based on 'Driver' Genes Independently Predicts Survival in a Validation Cohort The arrayCGH results described above implied that prognosis-related HCC subtypes may be biologically distinct. Building a survival prediction signature based on the 134 potential cancer 'driver' genes using Affymetrix gene expression data was sought. Class comparison analysis resulted in 10 significantly differentially expressed genes between G1 and G2 in cohort 1 (p<0.001; FDR<0.05; Table 4). Among these 10 genes, six genes mapped to 8p and were associated with poor survival while four genes mapped to 4q and were associated with good survival. Genomic locations and copy number of the 8p genes (DLC1, SH2D4A, SORBS3, CCDC25, ELP3 and PROSC) from a representative G2 case are shown in FIG. 3E. Quantitative RT-PCR of the 8p genes SH2D4A, CCDC25, DLC1, PROSC and SORBS3 showed high correlation with the microarray gene expression data (p<0.0001; FIG. 9).

TABLE 4

Class comparison analysis of G1 and G2 HCC subtypes by correlating aberrant genes in cohort 1

| Chromosome | Gene name | Fold-change [G2/G1] | Chromosome | Parametric p-value | Permutation p-value |
|---|---|---|---|---|---|
| 8p21.3 | SH2D4A | 0.58 | 8p21.3 | 1.31E−05 | <1e−07 |
| 8p21.1 | CCDC25 | 0.66 | 8p21.1 | 6.99E−05 | <1e−07 |
| 8p21.1 | ELP3 | 0.69 | 8p21.1 | 0.0006 | 0.0009 |
| 8p22 | DLC1 | 0.69 | 8p22 | 0.0003 | 0.0002 |
| 8p12 | PROSC | 0.71 | 8p12 | 0.0004 | 0.0005 |
| 8p21.3 | SORBS3 | 0.73 | 8p21.3 | 0.0004 | 0.0003 |
| 4q21.22 | HNRPD | 1.32 | 4q21.22 | 0.0003 | 0.0002 |
| 4q21.21 | PAQR3 | 1.47 | 4q21.21 | 0.0003 | 0.0004 |
| 4q28.2 | PHF17 | 1.53 | 4q28.2 | 0.0004 | 0.0005 |
| 4q13.3 | DCK | 1.63 | 4q13.3 | 0.0007 | 0.0006 |

A multivariate class prediction analysis using 10-fold cross validation was performed on cohort 1 cases (N=64) and then applied to predict 180 independent HCC cases in cohort 2. The 10-gene signature could significantly discriminate G1 from G2 cases in cohort 1 (multivariate cross-validated p<0.05). Similar to cohort 1, Kaplan-Meier survival analysis of cohort 2 revealed that the predicted G1 and G2 subgroups had significant survival differences (log-rank p=0.008; FIG. 4A). However, the 10-gene signature could not differentiate patient survival groups based on the corresponding non-tumor gene expression data (log-rank p=0.421; FIG. 4B). Similar results were observed with three additional class prediction algorithms. In addition, a survival-related gene signature could not be found when this search was restricted to non-correlated but somatically altered loci in HCC. Thus, the 10-gene signature was tumor-specific.

The Rho-GTPase activating protein Deleted in Liver Cancer 1 (DLC1) which was found in the 10-gene signature has been shown to be a functional TSG in HCC (Xue et al., Genes Dev. 22:1439-1444, 2008). To test whether DLC1 drove the predictive capacity of the 10-gene signature, class prediction was performed in the validation cohort after excluding this gene. Kaplan-Meier survival analysis showed that the 9-'driver' gene signature could equally well predict outcome (FIG. 10). Thus, DLC1 did not drive the predictive potential of this gene signature.

Next, Cox proportional hazards regression analysis was performed to determine whether the genomic predictor was confounded by underlying clinical parameters. Univariate analysis showed that the signature was a significant predictor of survival (p=0.004; Table 5). Multivariate analysis controlling for potential confounding covariates (serum AFP levels, cirrhosis and BCLC staging) demonstrated that the genomic predictor was significantly associated with a 2.1-fold increased risk of death for patients with a G2 gene aberration/expression profile (Table 5). Similar results were obtained for final models including CLIP or TNM staging. Thus, the HCC 'driver' gene signature is an independent and significant predictor of survival.

TABLE 5

Univariate and multivariate Cox regression analysis of clinical factors associated with overall survival[a]

| Clinical variable | Hazard Ratio (95% CI[b]) | P value |
|---|---|---|
| Univariate Analysis[c] | | |
| SVM predictor (G2 vs G1) | 2.4 (1.3-4.5) | 0.004 |
| Gender (Male vs Female) | 1.8 (0.9-3.8) | 0.102 |

TABLE 5-continued

Univariate and multivariate Cox regression analysis of clinical factors associated with overall survival[a]

| Clinical variable | Hazard Ratio (95% CI[b]) | P value |
|---|---|---|
| Age (>=50 years vs <50 years) | 0.8 (0.5-1.2) | 0.209 |
| AFP (>20 ng/mL vs <=20 ng/mL) | 1.7 (1.0-2.7) | 0.033 |
| ALT (>50 U/L vs <=50 U/L) | 1.2 (0.8-1.8) | 0.411 |
| Cirrhosis (Yes vs No) | 5.3 (1.3-21.7) | 0.019 |
| Tumor size (>5 cm vs <=5 cm) | 2.0 (1.3-3.0) | 0.001 |
| Multinodular (Yes vs No) | 1.7 (1.1-2.6) | 0.020 |
| HBV (AVR-CC vs CC)[d] | 1.4 (0.9-2.2) | 0.172 |
| Child Score (B vs A) | 1.3 (0.8-2.4) | 0.322 |
| BCLC staging (A vs 0) | 4.0 (1.0-16.4) | 0.056 |
| BCLC staging (B-C vs 0) | 12.9 (3.1-53.8) | <0.001 |
| CLIP staging (1 vs 0) | 1.5 (0.9-2.5) | 0.151 |
| CLIP staging (2-5 vs 0) | 3.8 (2.2-6.4) | <0.001 |
| TNM staging (II-III vs I) | 3.1 (1.9-5.2) | <0.001 |
| Multivariate Analysis[e] | | |
| SVM predictor (G2 vs G1) | 2.1 (1.1-4.0) | 0.021 |
| AFP (>20 ng/mL vs <=20 ng/mL) | 1.4 (0.8-2.2) | 0.203 |
| Cirrhosis (Yes vs No) | 4.0 (1.0-16.5) | 0.051 |
| BCLC staging (A vs 0) | 4.2 (1.0-17.4) | 0.048 |
| BCLC staging (B-C vs 0) | 12.2 (2.9-50.9) | 0.001 |

Bold indicates significant P values.
[a]Analysis was performed on the entire gene expression cohort (N = 244).
[b]95% CI, 95% confidence interval.
[c]Univarite analysis, Cox proportional hazards regression.
[d]AVR-CC (active viral replication chronic carrier); CC (chronic carrier).
[e]Multivariate analysis, Cox proportional hazards regression.

The 10-Gene 'Driver' Signature can Predict Survival in Breast Cancer

It was further tested whether the 10-gene signature was associated with survival of other solid tumors of an epithelial origin. The analysis was restricted to large cohorts with publicly available gene expression profiles using the same Affymetrix microarray platform and with available follow-up data. Six breast cancer datasets were identified, two (Uppsala-1 and Karolinska) with overall survival data and four with disease-free survival data (Uppsala-2, Rotterdam, Mainz and TRANSBIG) (Ivshina et al., *Cancer Res.* 66:10292-10301, 2006; Pawitan et al., *Breast Cancer Res.* 7:R953-R964, 2005; Desmedt et al., *Clin. Cancer Res.* 13:3207-3214, 2007; Wang et al., *Lancet* 365:671-679, 2005; Schmidt et al., *Cancer Res.* 68:5405-5413, 2008). Unsupervised hierarchical clustering was performed followed by Kaplan-Meier and Cox proportional hazard regression analyses based on the resulting subgroups. It was found that the 10-gene signature was significantly associated with overall survival in the Uppsala-1 and Karolinska cohorts and disease-free survival of the Uppsala-2 cohort, which were all composed of mixed node-positive and negative cases. However, the signature failed to predict disease-free survival in the Rotterdam, TRANSBIG or Mainz cohorts, which only contained node-negative cases suggesting that the survival predictive capacity of the 10-gene signature is associated with tumor cell dissemination (FIG. 4C). Taken together, the 10-gene set was validated in multiple independent cohorts as a signature to predict outcome of HCC patients and breast cancer patients with mixed node status.

Example 3

SORBS3 and SH2D4a Suppress HCC Tumor Growth In Vitro and In Vivo

Figure 11:
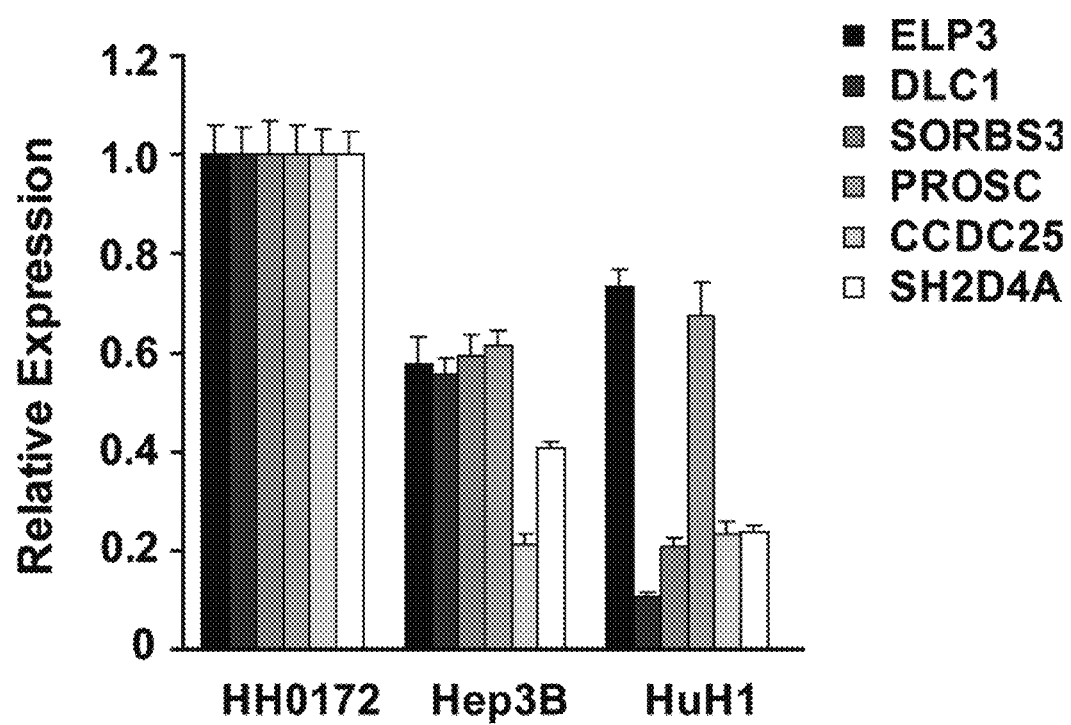
FIG. 11 is a graph showing ELP3, DLC1, SORBS3, PROSC, CCDC25 and SH2D4A gene expression in Hep3B and HuH1 cell lines.

Since DLC1, a known liver TSG, was identified in the 'driver' gene-panel associated with poor outcome, it was tested whether the remaining five genes on 8p (SH2D4A, SORBS3, CCDC25, ELP3 or PROSC) could act as HCC TSGs. It was hypothesized that if the screening approach led to TSG enrichment, a majority of the genes in the poor outcome signature would have the classic TSG impact of negative tumor cell growth. Thus, expression vectors encoding each of the six genes on 8p were introduced via transfection into Hep3B cells which harbor 8p deletions (Zimonjic et al., *Hepatology* 29:1208-1214, 1999) and into HuH1 cells which have reduced gene expression levels of all six genes (FIG. 11). The re-expression of PROSC, SORBS3 and SH2D4A inhibited HCC cell colony formation and cell migration in Hep3B and HuH1 cells (FIGS. 5A-5D). DLC1 was included as a positive control and the results were largely consistent with published data (Xue et al., *Genes Dev.* 22:1439-1444, 2008; Goodison et al., *Cancer Res.* 65:6042-6053, 2005; Zhou et al., *Int. J. Oncol.* 32:1285-1291, 2008). Thus, these results suggest a functional link between tumor cell growth and four of the six 'driver' genes on 8p.

Figure 6A:
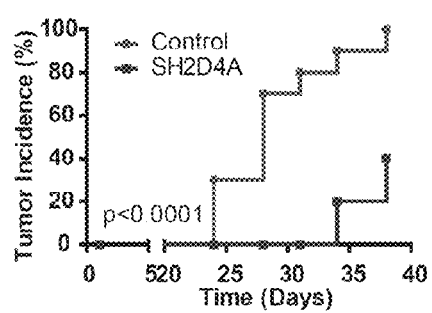
FIG. 6A is a graph showing tumor incidence of Hep3B cells transfected with vector control or SH2D4A cDNA after subcutaneous injection into immunocompromised mice (n=10).
Figure 6B:
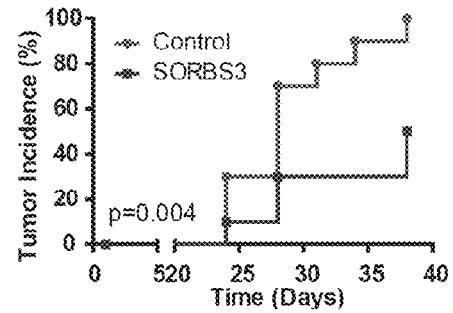
FIG. 6B is a graph showing tumor incidence of Hep3B cells transfected with vector control or SORBS3 cDNA after subcutaneous injection into immunocompromised mice (n=10). Tumor incidence was observed bi-weekly. The log-rank p-value is indicated.
Figure 6C:
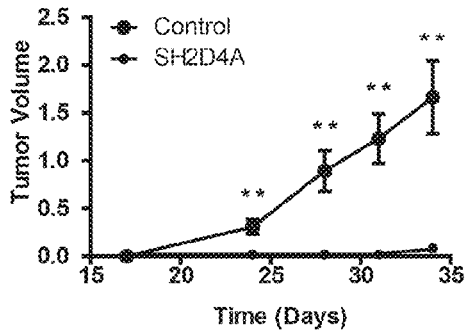
FIG. 6C is a growth curve of tumor xenografts of Hep3B cells transfected with vector control or SH2D4A (n=10).
Figure 6D:
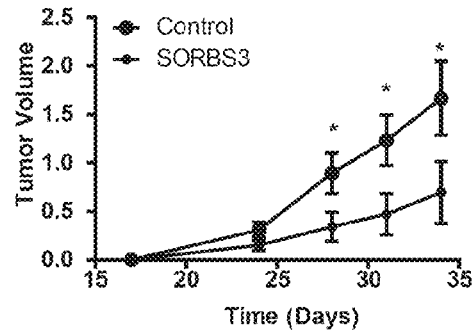
FIG. 6D is a graphs showing Xenograft tumor volumes of Hep3B cells transfected with vector control or SH2D4A (n=10). Data represent averages±SEM. *p<0.05, **p<0.005 by two-sided Student's t test.
Figure 12A:
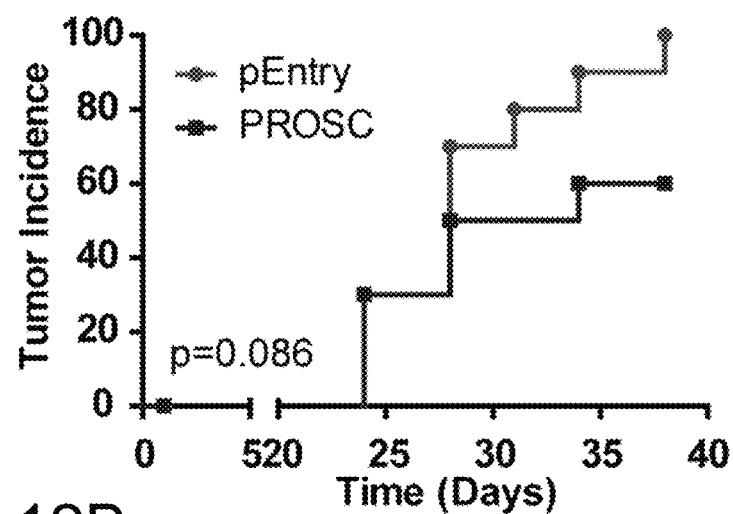
FIG. 12A is a graph showing tumor incidence of Hep3B cells transfected with vector control or PROSC cDNA after subcutaneous injection into immune-compromised mice (n=10).
Figure 12B:
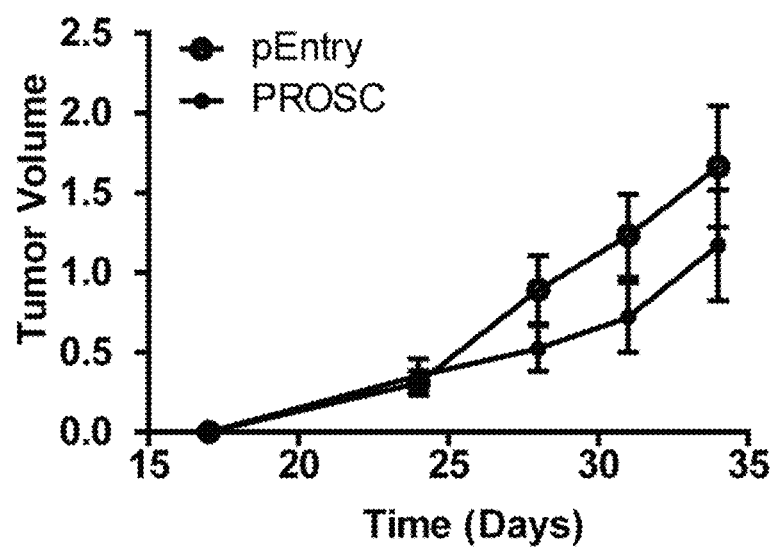
FIG. 12B is a graph showing tumor volume of Hep3B cells transfected with vector control or PROSC cDNA after subcutaneous injection into immune-compromised mice (n=10). Tumor incidence was observed bi-weekly. The log-rank p-value is indicated.
Figure 13:
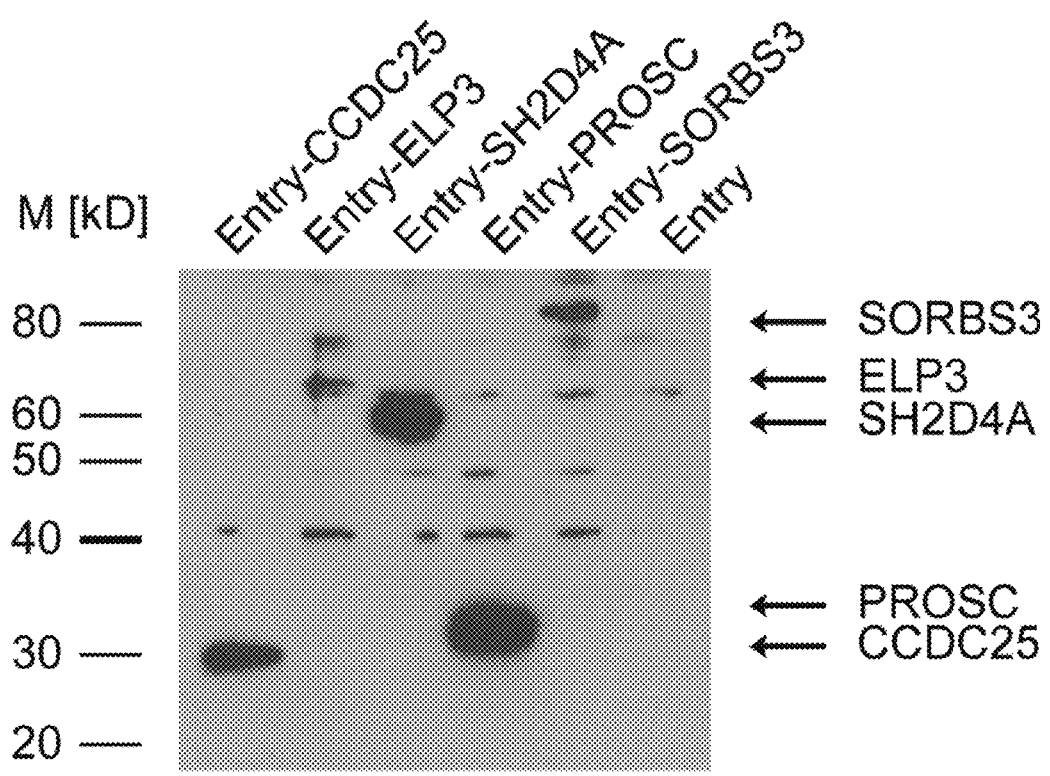
FIG. 13 is an immunoblot to test for the expression of the five potential tumor suppressor genes (TSGs). 293 cells were transfected with empty vector or vector encoding the five potential driver genes. Protein expression was detected by anti-flag immunoblot.

To examine the tumor suppressive function of PROSC, SORBS3 and SH2D4A in vivo, Hep3B cells transfected with PROSC, SORBS3, SH2D4A or the empty vector control were subcutaneously injected into immune-compromised nude mice. Expression of SH2D4A and SORBS3 significantly reduced the tumor incidence rate (FIGS. 6A and 6B) and the tumor volume (FIGS. 6C and 6D). PROSC expression also decreased tumor incidence rate and tumor volume, but the results were not statistically significant (FIG. 12). Taken together, these results indicate that loss of SH2D4A, SORBS3 and possibly PROSC contributes to HCC tumor growth and that their re-expression can inhibit HCC cell growth, migration and tumor initiation.

Example 4

Prognosis of Hepatocellular Carcinoma (HCC)

This example describes particular methods that can be used to prognose a subject diagnosed with HCC. However, one skilled in the art will appreciate that similar methods can be used.

A tumor sample and adjacent non-tumor sample is obtained from the subject's liver. Approximately 1-100 µg of tissue is obtained for each sample type, for example using a fine needle aspirate. RNA is isolated from the tumor and non-tumor tissues using routine methods (for example using a commercial kit).

In one example, the prognosis of a HCC tumor is determined by detecting expression levels of SH2D4A, CCDC25, ELP3, DLC1, PROSC, SORBS3, HNRPD, PAQR3, PHF17 and DCK in the tumor sample obtained from a subject by microarray analysis or real-time quantitative PCR. For example, the disclosed gene signature can be utilized. The relative expression level of SH2D4A, CCDC25, ELP3, DLC1, PROSC, SORBS3, HNRPD, PAQR3, PHF17 and DCK in the tumor sample is compared to the control (e.g., RNA isolated from adjacent non-tumor tissue from the subject). In other cases, the control is a reference value, such as the relative amount of such molecules present in non-tumor samples obtained from a group of healthy subject or HCC subjects. A decrease in expression of one or more of SH2D4A, CCDC25, ELP3, DLC1, PROSC, SORBS3, and/or an increase in expression of one or more of HNRPD, PAQR3, PHF17 and DCK, in the tumor sample relative to the control (such as a decrease or increase of at least 2-fold, at least 3-fold, or at least 5-fold) indicates a poor prognosis, such as a decrease in the likelihood of survival, for the subject.

In another example, the relative expression of HCC-associated molecules is determined at the protein level by methods known to those of ordinary skill in the art, such as protein microarray, Western blot or immunoassay techniques. Total protein is isolated from the tumor sample and control (non-tumor) sample and compared using any suitable technique. A decrease in protein expression of one or more of SH2D4A, CCDC25, ELP3, DLC1, PROSC, SORBS3, and/or an increase in protein expression of one or more of HNRPD, PAQR3, PHF17 and DCK in the tumor sample relative to the control (such as a decrease or increase of at least 2-fold, at least 3-fold, or at least 5-fold) indicates a poor prognosis, such as a decrease in the likelihood of survival, for the subject.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

The invention claimed is:

1. A method of treating HCC in a subject, comprising administering to the subject a therapeutically effective amount of an isolated nucleic acid molecule encoding a tumor-associated gene selected from the group consisting of SH2D4A and SORBS3, wherein the nucleic acid molecule is administered intratumorally.

2. The method of claim 1, wherein the nucleic acid molecule comprises a vector.

3. The method of claim 2, wherein the vector is a plasmid or a viral vector.

4. The method of claim 2, wherein the nucleic acid molecule encoding the tumor-associated gene is operably linked to a promoter.

5. A method of treating HCC in a subject, comprising administering to the subject a therapeutically effective amount of a vector comprising a nucleic acid molecule encoding SH2D4A or SORBS3 operably linked to a promoter, wherein the vector is administered intratumorally.

* * * * *